(12) United States Patent
Goyal

(10) Patent No.: US 12,194,252 B2
(45) Date of Patent: Jan. 14, 2025

(54) CATHETER REDIRECTION SYSTEMS FOR USE IN GAINING ACCESS TO CEREBRAL ARTERIES

(71) Applicant: MG Stroke Analytics Inc., Calgary (CA)

(72) Inventor: Mayank Goyal, Calgary (CA)

(73) Assignee: MG Stroke Analytics Inc., Calgary (CA)

(*) Notice: Subject to any disclaimer, the term of this patent is extended or adjusted under 35 U.S.C. 154(b) by 413 days.

(21) Appl. No.: 17/293,027

(22) PCT Filed: Dec. 9, 2020

(86) PCT No.: PCT/CA2020/051695
§ 371 (c)(1),
(2) Date: May 11, 2021

(87) PCT Pub. No.: WO2021/113970
PCT Pub. Date: Jun. 17, 2021

(65) Prior Publication Data
US 2022/0313953 A1    Oct. 6, 2022

Related U.S. Application Data

(60) Provisional application No. 62/945,432, filed on Dec. 9, 2019.

(51) Int. Cl.
*A61M 25/01* (2006.01)
*A61B 17/221* (2006.01)
(Continued)

(52) U.S. Cl.
CPC ....... *A61M 25/0147* (2013.01); *A61B 17/221* (2013.01); *A61M 25/0021* (2013.01);
(Continued)

(58) Field of Classification Search
CPC .. A61B 2017/2212; A61B 2017/22094; A61B 2017/22079; A61B 2017/22034;
(Continued)

(56) References Cited

U.S. PATENT DOCUMENTS

| 10,456,552 | B2 | 10/2019 | Goyal |
| 2004/0133232 | A1* | 7/2004 | Rosenbluth .......... A61B 17/221 606/200 |

(Continued)

FOREIGN PATENT DOCUMENTS

CA    3089554 A1    8/2019

OTHER PUBLICATIONS

"Analysis of Workflow and Time to Treatment and the Effects on Outcome in Endovascular Treatment of Acute Ischemic Stroke: Results in the SWIFT PRIME Randomized Controlled Trial" (Radiology. Jun. 2016;279(3):888-97. Doi: 10.1148/radiol.2016160204. Epub Apr. 19, 2016).

*Primary Examiner* — Tasnim Mehjabin Ahmed
(74) *Attorney, Agent, or Firm* — GrowIP Law Group LLC

(57) ABSTRACT

The invention describes catheter systems and methods for accessing the brain during endovascular/neurointervention procedures in the treatment of ischemic stroke. More specifically, a catheter system having a deployable redirection device (RD) is described that improves the process of accessing a clot in a patient with acute ischemic stroke due to large vessel occlusion.

13 Claims, 22 Drawing Sheets

(51) Int. Cl.
*A61M 25/00* (2006.01)
*A61B 17/22* (2006.01)

(52) U.S. Cl.
CPC ............... *A61B 2017/22034* (2013.01); *A61B 2017/22079* (2013.01); *A61B 2017/22094* (2013.01); *A61B 2017/2212* (2013.01); *A61M 2025/0042* (2013.01); *A61M 2210/0693* (2013.01); *A61M 2210/12* (2013.01)

(58) Field of Classification Search
CPC ............ A61B 17/221; A61M 25/0147; A61M 25/0021; A61M 2025/0042
See application file for complete search history.

(56) References Cited

U.S. PATENT DOCUMENTS

| | | |
|---|---|---|
| 2013/0035628 A1 | 2/2013 | Garrison et al. |
| 2016/0030709 A1 | 2/2016 | Losordo et al. |
| 2020/0163678 A1 | 5/2020 | Goyal |

\* cited by examiner

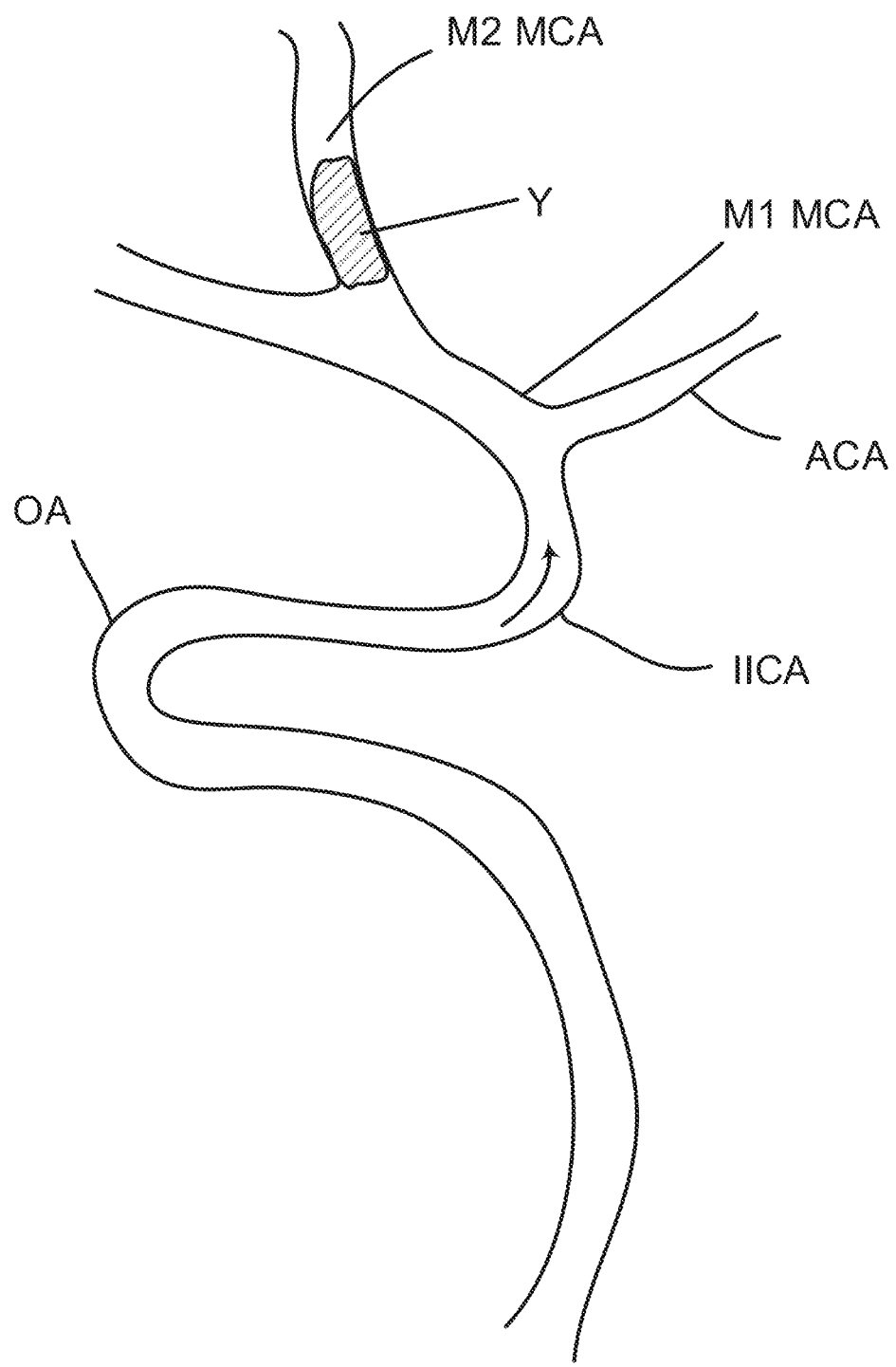
FIGURE 1A(1)

CATHETER REDIRECTION SYSTEMS FOR USE IN GAINING ACCESS TO CEREBRAL ARTERIES

CROSS REFERENCE TO RELATED APPLICATIONS

The present application claims the benefit of International PCT Patent Application No. PCT/CA2020/051695, filed on Dec. 9, 2020, that claims priority to U.S. Provisional Patent Application No. 62/945,432, filed on Dec. 9, 2019, the content of the foregoing applications is expressly incorporated herein by reference in its entirety.

FIELD OF THE INVENTION

The invention describes catheter systems and methods for accessing the brain during endovascular/neurointervention procedures in the treatment of ischemic stroke. More specifically, systems enabling improved control of a catheter through cerebral vessels are described that improve the process of accessing a clot in a patient with acute ischemic stroke due to large vessel occlusion.

BACKGROUND OF THE INVENTION

The human body is an extensive network of blood vessels including the venous and arterial systems for circulating blood throughout the body. The occurrence and/or development of restrictions to flow within the circulatory system can result in serious medical conditions, the most significant being myocardial infarction and ischemic stroke. The treatment of both conditions (and others involving the circulatory system) continues to evolve with many new techniques and equipment being utilized to effect treatment.

As is known, ischemic strokes caused by blood clot blockages in the brain may be treated by advancing catheter systems to the affected site whence various procedures can be initiated to treat the problem. Known techniques include the deployment of various designs of catheters singularly and/or in conjunction with other catheters/stents to gain access to and remove the clot.

When a patient experiences a significant ischemic stroke event, those portions of the brain distal to the occlusion that experience a dramatic reduction in blood supply will affect the functioning of large regions of neurons. This reduction in blood supply may cause the patient to become symptomatic, cause the death of regions of the brain and/or put regions of the brain at the risk of dying if not treated quickly. Depending on the location and size of the occlusion will result in a wide range of symptoms in the patient and depending on the severity will ultimately determine how a physician may choose to intervene or not.

Time delays in effecting treatment will typically result in the death of a greater number of neurons. Table 1 shows that in the specific case of acute ischemic stroke, the pace or rate of neural circuitry loss in a typical large vessel supratentorial acute ischemic stroke can be very rapid.

TABLE 1

Estimated Pace of Neural Circuitry Loss in Typical Large Vessel, Supratentorial Acute Ischemic Stroke
Estimated Pace of Neural Circuitry Loss in Typical Large Vessel, Supratentorial Acute Ischemic Stroke

|  | Neurons Lost | Synapses Lost | Myelinated Fibers Lost | Accelerated Aging |
| --- | --- | --- | --- | --- |
| Per Stroke | 1.2 billion | 8.3 trillion | 7140 km/4470 miles | 36 yrs |
| Per Hour | 120 billion | 830 billion | 714 km/447 miles | 3.6 yrs |
| Per Minute | 1.9 million | 14 billion | 12 km/7.5 miles | 3.1 weeks |
| Per Second | 32,000 | 230 million | 200 meters/218 yards | 8.7 hours |

The numbers presented above represent an average with it also being known that there is a high degree of variability in the above numbers generally depending on the available blood supply to the ischemic region through collateral channels. Several factors including time delays in making a decision, time delays in commencing an endovascular procedure and delays during the procedure, any of which may only be in the order of only a few minutes, can have a significant impact on neural circuitry loss and ultimately patient outcome.

The paper "Analysis of Workflow and Time to Treatment and the Effects on Outcome in Endovascular Treatment of Acute Ischemic Stroke: Results from the SWIFT PRIME Randomized Controlled Trial" (Radiology. 2016 June; 279 (3):888-97. doi: 10.1148/radiol.2016160204. Epub 2016 Apr. 19), and incorporated herein by reference, quantitatively shows that there is a definitive improvement in patient outcome through fast reperfusion. In particular, this study concluded that "aggressive time goals may have contributed to efficient workflow environments". Further, the study quantifies inter alia that functional independence of a patient was significantly higher when treated quickly (i.e. within 2.5 hours of stroke onset).

Importantly, it is now known that efficient workflows during a recanalization procedure (of which the effectiveness and efficiency of a procedure is important) provides better outcomes.

Initially, in diagnosing ischemic stroke to assess possible treatments, it is important for the physician to know where the vessel occlusion is, how big the occlusion is, where any dead brain tissue ("core") is and, how big and where is the brain tissue that may have been affected by the ischemic event but that may potentially be saved ("penumbra").

The penumbra is tissue around the ischemic event that can potentially stay alive for several hours after the event by the perfusion of this tissue by collateral arteries. The collateral arteries may provide sufficient oxygen, nutrients and/or flushing to the penumbra tissue to prevent this tissue from dying for a period of time.

When responding to acute ischemic stroke, endovascular treatment of acute ischemic stroke due to large vessel occlusion in the anterior circulation is now the standard of care for patients under certain criteria. That is, patients exhibiting particular symptoms (i.e stroke symptoms of a particular severity) will benefit from early and rapid endovascular intervention to open occluded blood vessels. Generally, during various endovascular treatments, an interventionist will advance a series of catheters from the patient's groin through the femoral artery, descending aortic artery, to the aortic arch and into the cervical and cerebral arterial system towards the clot. After access to the clot is achieved by placement of the catheters, clot-retrieval and/or clot-suction devices are deployed through the catheter where the clot is either withdrawn and/or aspirated from the clot site.

There are many anatomical and situational considerations that can affect the severity and ultimately treatment of ischemic stroke. Importantly, as described above, while a blood clot may severely affect blood flow to the ischemic area, some blood flow may get to the ischemic area if collateral arteries are functioning to at least partially perfuse the affected area.

The most common large vessel occlusion that is treated by endovascular techniques is the M1 segment of the middle cerebral artery (MCA). When a patient has an M1 occlusion, the territory supplied by the M1 receives a dramatic reduction in blood supply. As a consequence, distal neurons don't function well and the patient becomes symptomatic.

Recanalization procedures utilize a wide range of equipment and techniques to access a clot and effect its removal. Generally, the endovascular surgeon will have several tools at their disposal including a wide range of guide catheters, balloon guide catheters, diagnostic catheters, microcatheters, microwires, stents and other tools that individually have properties, features and functions that are effective for different procedures and patient presentations. Most, if not all, of the above tools are disposable and they are also expensive. Hence, to the extent that similar or better results can be achieved utilizing faster procedures (i.e. in fewer steps), a smaller number of tools and/or at a lower cost, there is a motivation to continue to design new tools that can achieve these objectives.

Typically, these procedures are performed by gaining access to the arterial vascular system through the patient's groin area by puncturing the common femoral artery. An arterial sheath is inserted.

Then, under fluoroscopic (Xray) guidance, a catheter system (usually a co-axial system including a guide catheter or balloon guide catheter and diagnostic catheter) is advanced through the descending aorta to reach the aortic arch.

The diagnostic catheter is shaped and is used to hook the vessel of interest and with the help of a guidewire, the diagnostic catheter is advanced to the relevant carotid artery. Subsequently the guide catheter/balloon guide catheter) is advanced over the diagnostic catheter such that the tip is in the relevant internal carotid artery.

At this stage, the diagnostic catheter and wire are removed.

Subsequently, catheters that are designed for intracranial access are advanced through the guide catheter. This will typically consist of one of two approaches:
 a. a microcatheter and a microwire; or,
 b. a tri-axial system comprising of a distal access catheter (DAC), a microcatheter and a microwire.

For approach a: once the clot has been crossed by the microcatheter and microwire, the microwire is removed and a stent-retriever is slowly deployed across the clot. While aspirating through the guide catheter (with the balloon inflated if using a BGC) the stent-retriever is withdrawn to capture the clot and establish reperfusion.

For approach b: the DAC is placed proximal to the clot. In approach b1: the microcatheter is used to cross the clot and after removal of the microwire, a stent retriever is deployed. Then the stent-retriever and DAC are typically withdrawn together, while aspirating from the DAC. In approach b2: a stent retriever is not used and directly an attempt is made to capture the clot by aspirating through the DAC.

All of these approaches require accessing the carotid artery through the aortic arch.

It is known that stroke typically affects the elderly and with increasing age, there is usually an increase in tortuosity of the aortic arch making it tough to access the carotid artery. In particular, a highly tortuous combination of aortic arch and carotid artery can be difficult to advance catheter systems through as high bend angles and friction may cause catheters to prolapse into the ascending aorta and thus fail to advance through the desired vessel. In other words, when pushing a catheter system through tight bends, the system may seek the path of least resistance and can end up being pushed in a wrong direction. In addition, tortuosity may prevent further advancement of the catheter. The combination of a sharp turn and an origin of another artery, as is commonly seen in the ophthalmic segment of the internal carotid artery can be a common place where such a catheter can get stuck.

Catheter Performance

As mentioned above, there are generally two classes of catheters used in cerebral procedures namely diagnostic and guide catheters. Diagnostic catheters are generally those used to gain access to an area of interest whereas guiding catheters are used to support and guide additional equipment including diagnostic catheters, guidewires, balloons, other catheters etc. as may be required for a particular surgical technique.

Typical diagnostic catheters will range from 4 F to 6 F (French) and have lengths of 65-125 cm. They may have braided wall structures and they will generally have a soft tip with a range of shapes formed into the tip.

Guide catheters are generally larger (e.g. 6-8 F) and are 80-100 cm in length. They generally have reinforced construction with a significantly stiffer shaft to provide back-up (i.e. retro) support for the advancement of any additional equipment as listed above. However, guide catheters can generally only be advanced as far as the carotid artery in the neck in that the combination of their stiffness, the narrowing of vessels and the curvature of vessels prevents further advancement.

From an anatomical perspective, catheters generally pass through different zones of the vasculature, namely the abdominal and thoracic vasculature between the femoral artery and aortic arch (approximately 50-75 cm), the cervical vasculature (approximately 15-20 cm) and the cephalic/cerebral vasculature (approximately 10-15 cm). The vessels progressively narrow from 2 cm in the aorta down to 3 mm and smaller in the cerebral vessels.

Various properties and geometries may be engineered into both diagnostic and guide catheter including:
 Trackability—the ability of the catheter to slide over a guide wire particularly through tortuous (tightly curved) vessels.
 Pushability—the ability to advance the tip or head of the catheter based on the input from the operator from the hub (i.e. from outside the body).
 Torquability—the ability to steer the tip of the catheter based on twisting at the hub by the operator.

Tip or head shape—the shape of the tip or head of the catheter will assist the operator in navigating the distal tip of the catheter through particular anatomical features. For example, a diagnostic catheter may have a flush, straight, simple curve, complex curve, reverse curve or double curve shapes inter alia. Such shapes may be categorized as simple or complex.

Stiffness—the ability of a catheter to bend around a curve and support a catheter moving within it.

In particular, and as noted above, diagnostic catheters are provided with a wide range of tips having the above shapes to allow the interventionist a choice of tip shape when conducting a procedure mainly to address variations in a patient's anatomy.

Catheter Construction

Each catheter may be constructed from a plurality of materials, having various structures and/or layers within the catheter wall structure to give the catheter particular properties or functional characteristics. These may include:

Surface Coatings—Surface coatings desirably reduce thrombogenicity, have low friction coefficients and/or anti-microbial characteristics.

Reinforcement—Internal wire braiding is used to impart torque control/stiffness characteristics to the catheter.

Polymer Layers—Different polymers may be used to give different structural characteristics to the body of the catheter. For example, Polyurethanes can be soft and pliable and hence follow guide wires more effectively. However, they have a higher coefficient of friction.

Nylon may be used for stiffness and be able to tolerate higher flow rates of fluids through them.

The choice of a particular catheter or system of catheters is typically determined by the skill, experience and preferences of a particular interventionist.

Some typical properties of different catheters are summarized in Table 2.

TABLE 2

Summary of Catheter Properties

| Catheter | Body Properties | Diameter | Typical Length | Typical Tip Features |
| --- | --- | --- | --- | --- |
| Guide Catheter | Usually quite stiff Atraumatic tip Supports and guides other catheters Double lumen if Balloon Guide Catheter (BGC) | 6-8 F | Extracorporeal + Groin to Carotid 80-100 cm | May have balloon |
| Diagnostic Catheter | Variable Tip Stiffness Variable Tip Shapes Torquable | 4-6 F | Extracorporeal + Groin to Carotid 100-125 cm | Soft Tip Multiple Shapes |
| Microcatheter | Soft Tip Pushable Trackable | 1-5-2.5 F | Goes through the guide catheter Travel to intracranial vessels (over a microwire) and to beyond the clot. 150 cm | Rounded Soft Tip |
| Guide Wire | Pushable Torquable | 1 F | Travels inside of diagnostic catheter or guide catheter (used to advance these catheters to the cervical carotid artery) 150-300 cm | Rounded |
| Reperfusion Catheter | Multizone (may be up to 12-15 zones) Increasing level of softness distally to allow the catheter to negotiate significant tortuosity and remain atraumatic Distal transition zones may extend for | 4-6 F (diameter may be more proximally to allow for better suction. | Travel inside the guide catheter. Usually over a microcatheter Extracorporeal + Groin to Occlusion 105-125 cm | Rounded Soft Tip Challenging design to prevent ovalization during passing through significant curvature and while applying suction. |

TABLE 2-continued

Summary of Catheter Properties

| Catheter | Body Properties | Diameter | Typical Length | Typical Tip Features |
|---|---|---|---|---|
| | 30-40 cm) Enables two-way Fluid Flow Pushable | | | |
| Stent | Integrated Clot Retrieval System Pushable | very small in its collapsed state (travel through microcatheter). In expanded state: 3-6 mm | Extracorporeal + Groin to Occlusion 180 cm Travel through microcatheter. | Integrated Clot Retrieval System |
| Microwire | Pushable Torquable 10-16/1000 of an inch soft atraumatic tip | 180-200 cm travels through microcatheter | extracorporeal to intracranially (beyond the clot) | round soft tip. |

Typical Endovascular Procedures for Treatment of Ischemic Stroke

As noted above, when an endovascular surgeon begins a procedure, access to the vasculature is typically obtained through the groin. After groin puncture, a variety of the following steps are performed to advance different catheters through the vasculature to a site of interest. Typically, in the case of a procedure using a balloon guide catheter and stent (i.e a clot retrieval device), these steps include:

Step A—Aortic Arch Access

Following groin puncture, a sheath is deployed. The sheath acts as an access port to the body and will be inserted about 5 cm of a typical 15 cm length into the femoral artery. The sheath has an ID of approximately 8 F.

An assembly of a guide catheter (GC)/balloon guide catheter (BGC), a diagnostic catheter (DC) and guide wire (GW) is advanced to the aortic arch. The GC/BGC will typically have an OD of 8 F. The DC (OD 4-6 F) is retained inside the BGC and the GW (OD 0.035″) is retained within the DC.

Step B—Carotid and Cerebral Artery Access

The DC is manipulated to gain access to the desired carotid artery.

After gaining access to the carotid artery, the GW is advanced, typically up to 20-30 cm towards the occlusion site (but within the cervical carotid arteries).

After the GW has been advanced (or concurrently and/or sequentially), the DC is advanced over the GW to gain access to the occlusion site. This may occur in a concurrent and/or sequential process depending on the particulars of a particular patient. However, this step can have significant problems. The design of the DC is to enable hooking the relevant vessel. Typically, the tip (distal 5 cm) is pre-shaped and overall the diagnostic catheter is stiff and torquable. These properties make it possible to hook the vessel but actually work against the interventionist as one proceeds to advance the DC over the wire as often the whole system prolapses into the ascending aorta. An alternative approach is to not advance the DC but instead advance the BGC while leaving the DC in position at the origin of the vessel. This solution does work sometimes but often also has the same problem due to the stiffness of the guide catheter.

Step C—Guide Catheter (GC)/Balloon Guide Catheter (BGC) Placement

The GC/BGC is advanced over the DC and GW to also gain access to a straight segment of the cervical internal carotid artery.

The DC and GW are then fully removed.

Step D—Microcatheter/Microwire Placement

A microcatheter (MC) and microwire (MW) are advanced together through the BGC all the way to the clot such that the distal tip of the MC and MW are positioned just past the distal edge of the clot. A MC as described in Applicant's copending application U.S. Ser. No. 14/809,867 and incorporated herein by reference, may be used to effect movement through these arterial systems.

Once the MC is positioned, the MW is removed.

Step E—Stent Deployment

A stent (i.e. clot retrieval device) is advanced through the MC until the distal tip of the stent is adjacent the distal end of the MC.

The stent is unsheathed by pulling back on the MC while holding the stent in position. As the stent is unsheathed it will expand into clot to engage with the clot.

Step F—Clot Removal

The BGC is inflated to stop ante grade flow and retrograde flow (suction) through the BGC is initiated.

Simultaneously, the stent which is now engaged with the clot, together with the MC is pulled proximally through the BGC to outside of the body.

A check angiogram is performed through the BGC to see if the clot retrieval has been successful. If not the steps j-m may be repeated again.

Once successful reperfusion has been achieved the BGC, stent and clot are removed from the body.

Variations

In variations of the procedure, a distal access catheter (DAC) (4-6.5 F) may be added to the procedure. This can be done one of two ways Aspiration technique.

i. In this technique, after access to the cervical internal carotid artery has been achieved using a guide catheter and DC, the guide catheter (GC) which is not a BGC (i.e. a DAC) is placed in the cervical internal carotid artery.

ii. The DC is removed
iii. A tri-axial system consisting of a DAC, a MC and MW are advanced towards the intracranial circulation with the aim of having the tip of the DAC (Aspiration catheter) reach the face of the clot. For achieving this it is possible that the MC and MW may have to be placed beyond the clot. Typically, in this case, the DAC will have a maximum size of 6 F. Bigger size catheters are usually not possible as they would need bigger guide catheters in the neck and and/or negotiating through the curves becomes tougher.
iv. The MW and MC are removed.
v. With the DAC at the face of the clot, suction through the DAC is applied until there is successful retrieval of clot or the endovascular surgeon decides to try an alternative approach. Local suction has an advantage that more of the suction pressure is likely to be transmitted to the clot. However, as described below, there are several possible outcomes when aspiration is applied.

Solumbra technique
i. The initial part of this technique is the same as the Aspiration technique (i.e steps a(i)-a(iii)).
ii. However, once the MC is beyond the clot and the DAC is at the face of the clot, the MW is removed and a stent is deployed across the clot.
iii. Then, while applying suction to the DAC, the MC and stent are withdrawn. Thus, the suction pressure is right next to the clot rather than from the neck as with a BGC. Also, the stent enters the DAC while still in the intracranial vessels thus reducing the likelihood of losing the clot once it has been captured.

In cases where the aspiration techniques without using a stent are not successful in removing the clot, with a BGC in place, a GW, MC and stent may be subsequently deployed.

In both techniques, the application of suction pressure can result in a variety of outcomes. Generally speaking, typical DACs (aspiration catheters) will be smaller than most clots where the DACs will have a maximum ID in the range of 0.068-0.075" (with corresponding ODs of approximately 0.075-0.082") whereas the size/OD of the clot will be effectively the same as the ID of the vessel that it lodges in. Thus, there will be a difference between the size of the distal tip opening of the DAC and the clot. As a result, in cases where the clot is "significantly" larger than the DAC, aspiration through the distal tip of the DAC will generally not achieve ingestion of the clot but rather the proximal most part of the clot gets 'corked' into the distal tip of the DAC. Most clots are not that compressible.

Importantly, as the properties of the clot are highly variable in terms of consistency/rigidity/internal cohesion etc., the ultimate application of suction and/or proximal pressure may result in:

The entirety of the clot being ingested into the DAC (desired).

The clot partially breaking into one or more smaller pieces and proximal piece(s) being fully ingested into the DAC which may result in piece(s) moving distally (not desired).

The clot not being ingested into the DAC and plugging the distal tip thus requiring the DAC to be withdrawn with the clot only partially ingested (favorable end result but may not be rapid).

As in c. fibrin rich zones of the clot may get stuck in the DAC requiring withdrawal of the DAC to remove a section of the clot. In some cases, the clot may also have less fibrin rich zones which can then break away from the stuck part with smaller piece(s) then moving further distally (not desirable).

The clot not fully engaging with the DAC and/or not being ingested resulting in the clot remaining where it is (which may then cause the surgeon to consider deploying a stent; less desirable).

Overall, of all these possibilities, completion ingestion of the clot is the most desirable as this a) prevents fragmentation, b) distal emboli and c) as the more proximal part of the clot gets sucked into the catheter, the suction pressure gets transmitted to the next portion of the clot. However, as noted above DACs have generally had an upper limit in size which can thus result in a higher mismatch of sizes between the vessel/clot and the DAC.

Furthermore, once a clot is believed to have been captured, it is generally necessary to fully withdraw the DAC from the body to enable a check angiogram to be conducted. The check angiogram is conducted to determine if the clot has been fully removed and to determine if any smaller pieces have been left behind.

As noted, BGCs are used to enable the surgeon to stop ante grade blood flow and are necessary to minimize the risk in cases where the DAC is being withdrawn with a partially-ingested clot for the clot to shear and embolize distally. That is, as the diameter of the clot (and stent if being used) can be larger than the inner lumen of the BGC, as the DAC is being withdrawn (with or without the stent), there is a significant chance of part of the clot being sheared off and embolizing distally. Hence cessation of ante grade flow by inflating the balloon reduces the risk of this happening. However, the use of a BGC reduces the size of the DAC as the DAC must be within the BGC.

Hence, advancing a single large ID/OD catheter from the groin (or other access point) to the clot without using a BGC is desirable. More specifically, it is desirable to position a larger catheter having larger distal opening deeper in the brain to:

fully engage and improve the ability to ingest the blood clot reduce the time to complete an aspiration procedure reduce the cost of conducting an aspiration procedure reduce the risk of dislodging or pushing a clot deeper into the brain as a catheter is being advanced.

For example, as described in Applicant's U.S. Pat. No. 10,456,552, systems are described (referenced as the '552 system) that can be used to ease an aspiration catheter through tight curves. The '552 system functions as a microcatheter that has a distal tapered section that can be positioned adjacent the distal tip of a larger catheter to help guide the distal tip of the larger catheter around a curve. A drawback of this system can occur when the clot is located close to the tortuous section (i.e. immediately downstream) which can prevent the physician from choosing to use the '552 system as the physician may determine that the distal tip of the '552 system may push against the clot which could dislodge the clot.

Another issue in advancing catheters into the brain through tortuous sections is the potential build-up of stress in the catheters as they are pushed and twisted into position. Specifically, as a catheter is advanced and may become stuck, the surgeon will have imparted various compressive and/or torque forces onto the catheter. If the distal tip has become stuck, there may be unreleased elastic forces within the catheter that may be suddenly released and cause the catheter to jump forward which increases the risk of the distal tip of the catheter suddenly engaging with the clot and dislodging it.

A further problem can occur when a clot is located at or near a vessel bifurcation and alignment of an aspiration catheter with the clot is more difficult.

SUMMARY OF THE INVENTION

In accordance with a first aspect, the invention provides a method for advancing an aspiration catheter (AC) through a tortuous section of a cerebral artery, particularly when the AC has become stuck within the tortuous section, the method comprising the steps of: a) conveying a redirection device (RD) operatively retained within a microcatheter (MC) through the AC to a distal tip of the AC, the MS having a push wire (PW) operatively connected to a proximal end of the RD wherein the RD is expandable relative to the size of the MC; b) conveying the MC and RD to a position beyond the distal tip of the AC; c) withdrawing the MC relative to the RD so as to cause a distal tip of the MS to emerge from the MC and expand to engage with an inner wall of the cerebral artery and the distal tip of the AC and wherein contact of the RD with both the cerebral artery and AC relieves pressure on the distal tip of the AC preventing forward movement of the AC; and, d) when pressure has been relieved and/or the AC has been re-aligned with the cerebral artery, advancing the AC forward over the RD.

In various aspects, the method may also include steps of re-sheathing the RD within the MC; and, withdrawing the RD and MC from the AC.

The method may also include advancing a MC operatively containing a microwire (MW) within the AC to provide support to the AC for further advancement of the AC within the cerebral artery.

In another aspect, the invention provides a method for advancing an aspiration catheter (AC) through a tortuous section of a cerebral artery, particularly when the AC has become stuck within the tortuous section, the method comprising the steps of: a) conveying a redirection device (RD) operatively retained within the AC to a distal tip of the AC, the RD having a push wire (PW) operatively connected to a proximal end of the RD wherein the RD is expandable relative to the size of the AC; b) pushing the RD to a position beyond the distal tip of the AC so as to cause a distal tip of the RD to emerge from the AC and expand to engage with an inner wall of the cerebral artery and the distal tip of the AC and wherein contact of the RD with both the cerebral artery and AC relieves pressure on the distal tip of the AC preventing forward move of the AC; and, c) when pressure has been relieved and/or when the AC has been re-aligned within the cerebral artery, advancing the AC forward over the RD.

In another aspect, the invention provides a system for relieving pressure and re-aligning an aspiration catheter (AC) in contact with a cerebral artery, particularly within a tortuous section of the cerebral artery comprising: a redirection device (RD) operatively contained within a microcatheter, the RD expandable and having a microwire (MW) operatively connected to a proximal end of the RD wherein the RD is deployable and re-sheathable from a distal tip of the MC and wherein upon deployment the RD is expandable to engage with an inner wall of the cerebral artery and a distal tip of the AC to relieve contact pressure between the AC and cerebral artery and/or re-align the AC within the cerebral artery.

The RD may be self-expanding or be manually expandable and compressible.

In various embodiments, the system includes a first MW fixed to a proximal end of the RD and a second MW fixed to a distal end of the RD, the second MW being telescopically retained within the RD and where movement of the first MW relative to the second MW causes shortening or lengthening of the RD to cause expansion and compression of the RD respectively.

In one embodiment, a first MW is operatively connected to a proximal end of the RD and a second MW is telescopically retained within the RD and is operatively engageable with a distal tip of the RD and where movement of the first MW relative to the second MW causes a shortening or lengthening of a distance between the proximal and distal ends of the RD and causes an expansion or compression respectively of a diameter of the RD.

In another embodiment, the second MW can be advanced and torqued relative to the RD and the second MW includes a DES distal to the MW, the DES engageable with the distal end of the RD.

In another embodiment, the second MW includes a distal tip portion distal to the RD.

In another aspect, the invention provides a system for relieving pressure and re-aligning an aspiration catheter (AC) in contact with a cerebral artery, particularly within a tortuous section of the cerebral artery comprising: a redirection device (RD) operatively contained within a microcatheter, the RD self-expanding and having a microwire (MW) operatively connected to a proximal end of the RD wherein the RD is deployable and re-sheathable from a distal tip of the MC and wherein upon deployment the RD expands to engage with an inner wall of the cerebral artery and a distal tip of the AC to relieve contact pressure between the AC and cerebral artery and/or re-align the AC with the cerebral artery.

In another aspect, the invention provides a method for redirecting and advancing an aspiration catheter (AC) past a cerebral artery at a bifurcation and retrieving a clot adjacent the bifurcation, the method comprising the steps of: conveying a redirection device (RD) operatively retained within a microcatheter (MC) through the AC to a distal tip of the AC, the RD having a push wire (PW) operatively connected to a proximal end of the RD wherein the RD is expandable relative to the size of the MC; conveying the MC and RD to a position beyond the distal tip of the AC and past a distal edge of the clot; withdrawing the MC relative to the RD to cause a distal tip of the RD to emerge from the MC and expand to engage with the clot and the distal tip of the AC and wherein contact of the RD with the AC relieves pressure on the distal tip of the AC preventing forward movement of the AC; when pressure has been relieved and/or the AC has been re-aligned with the cerebral artery, advancing the AC forward over the RD to a proximal edge of the clot; and, applying suction and withdrawing all of the RD, MC and AC.

BRIEF DESCRIPTION OF THE DRAWINGS

Various objects, features and advantages of the invention will be apparent from the following description of particular embodiments of the invention, as illustrated in the accompanying drawings. The drawings are not necessarily to scale, emphasis instead being placed upon illustrating the principles of various embodiments of the invention. Similar reference numerals indicate similar components.

FIG. 1A(1) is a schematic diagram of a region of the cerebral vasculature showing a clot Y adjacent a bifurcation.

DETAILED DESCRIPTION

Rationale

Figure 1A:
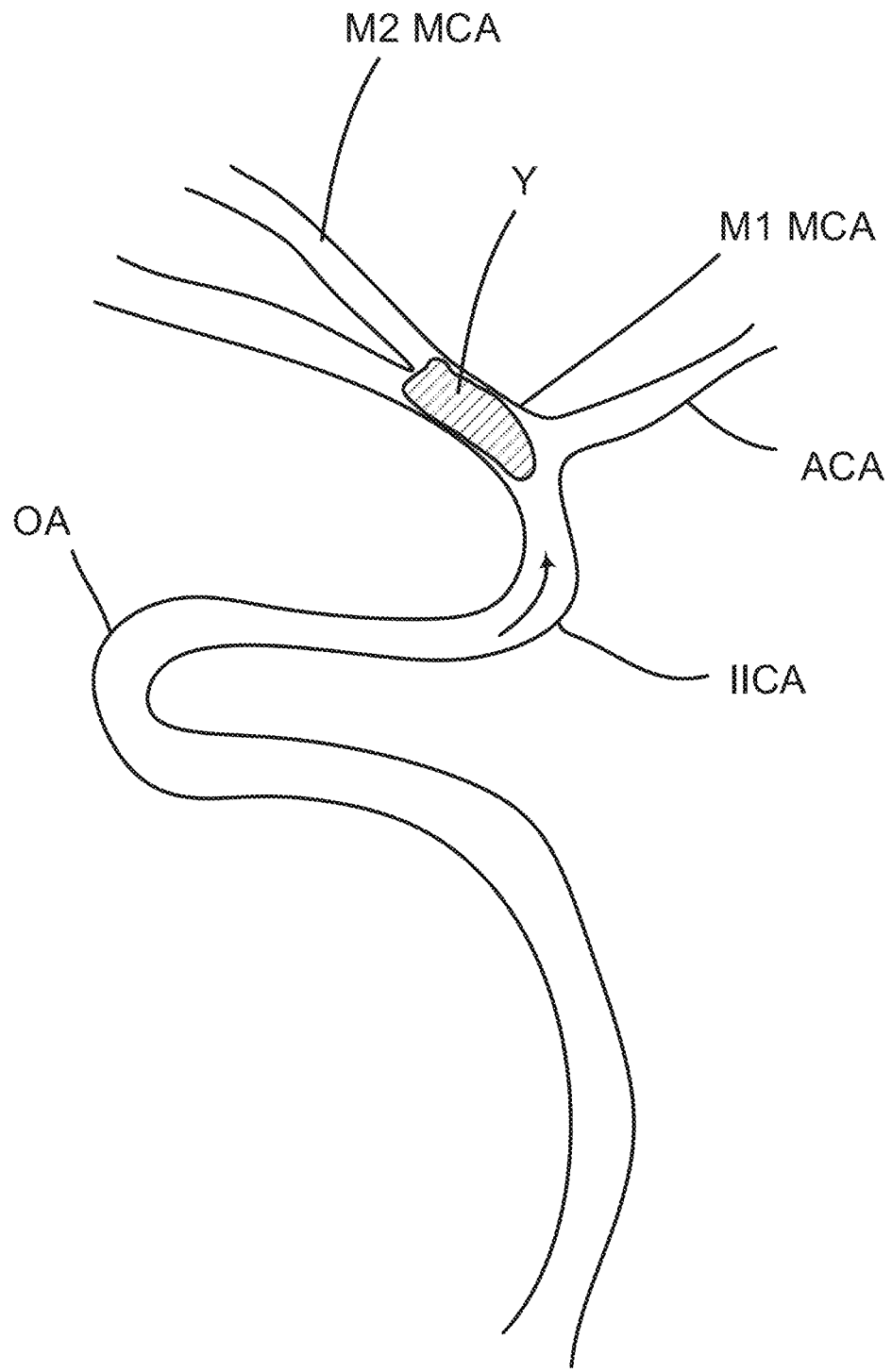
FIG. 1A is a schematic diagram of a region of the cerebral vasculature showing a clot Y distal to a tortuous section of the vasculature.

The inventor who has experience in the treatment of acute ischemic stroke recognized that a problem exists in moving larger diameter aspiration catheters through the cerebral vasculature and in particular the problem of such catheters getting stuck within the cerebral arteries during advancement of the catheter towards a clot. The invention as described herein, describes procedures and systems for relieving pressure on a stuck aspiration catheter and otherwise re-aligning the catheter within an artery to enable it to be advanced further during endovascular/neuro-intervention procedures.

Scope of Language

Introduction

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Spatially relative terms, such as "distal", "proximal", "forward", "rearward", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a feature in the figures is inverted, elements described as "under" or "beneath" other elements or features would then be oriented "over" the other elements or features. Thus, the exemplary term "under" can encompass both an orientation of over and under. A feature may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present.

It will be understood that, although the terms "first", "second", etc may be used herein to describe various elements, components, etc., these elements, components, etc. should not be limited by these terms. These terms are only used to distinguish one element, component, etc. from another element, component. Thus, a "first" element, or component discussed herein could also be termed a "second" element or component without departing from the teachings of the present invention. In addition, the sequence of operations (or steps) is not limited to the order presented in the claims or figures unless specifically indicated otherwise.

Other than described herein, or unless otherwise expressly specified, all of the numerical ranges, amounts, values and percentages, such as those for amounts of materials, elemental contents, times and temperatures, ratios of amounts, and others, in the following portion of the specification and attached claims may be read as if prefaced by the word "about" even though the term "about" may not expressly appear with the value, amount, or range. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Unless otherwise defined, all technical and scientific terms used herein have the same meaning as commonly understood by one of ordinary skill in the art to which this invention belongs.

Various aspects of the invention will now be described with reference to the figures. For the purposes of illustration, components depicted in the figures are not necessarily drawn to scale. In particular, as the scale of catheter components is relatively small in the width direction (typically a few mm) compared to the length direction (typically cm+), in the drawings, for illustrating key concepts, the width may appear substantially wider than it might otherwise appear in reality in several drawings. Instead, emphasis is placed on highlighting the various contributions of the components to the functionality of various aspects of the invention. A number of possible alternative features are introduced during the course of this description. It is to be understood that, according to the knowledge and judgment of persons skilled in the art, such alternative features may be substituted in various combinations to arrive at different embodiments of the present invention.

FIG. 1A shows a schematic section of the cerebral arteries where access to a blood clot Y is required distal to a tortuous section of the vasculature. In this case, the clot Y is located in a location distal to the ophthalmic artery which is typically a location that is difficult to negotiate with larger catheters, particularly in older patients.

As described in the inventor's co-pending applications U.S. provisional application 62/878,652, filed Jul. 25, 2019, U.S. provisional application 63/029,401 filed May 23, 2020 and PCT International application PCT/CA2020/051026 filed Jul. 24, 2020, and incorporated herein by reference, catheters designed to extend from the access position (typically the groin or radial arteries) can be used as aspiration catheters if they can be advanced sufficiently close to the clot to enable aspiration. Such catheters, after gaining access to the carotid arteries, are advanced via progressive advancement of a microwire MW and microcatheter MC followed by the larger catheter that is to be used for aspiration. This larger catheter is referred to as either a G2B (groin to brain) catheter to utilize consistency with terminology used in other applications and also an aspiration catheter (AC). Generally, it is understood that this terminology is for convenience only and other catheters having different entry points (eg. the radial or brachial artery) are contemplated.

Figure 1B:
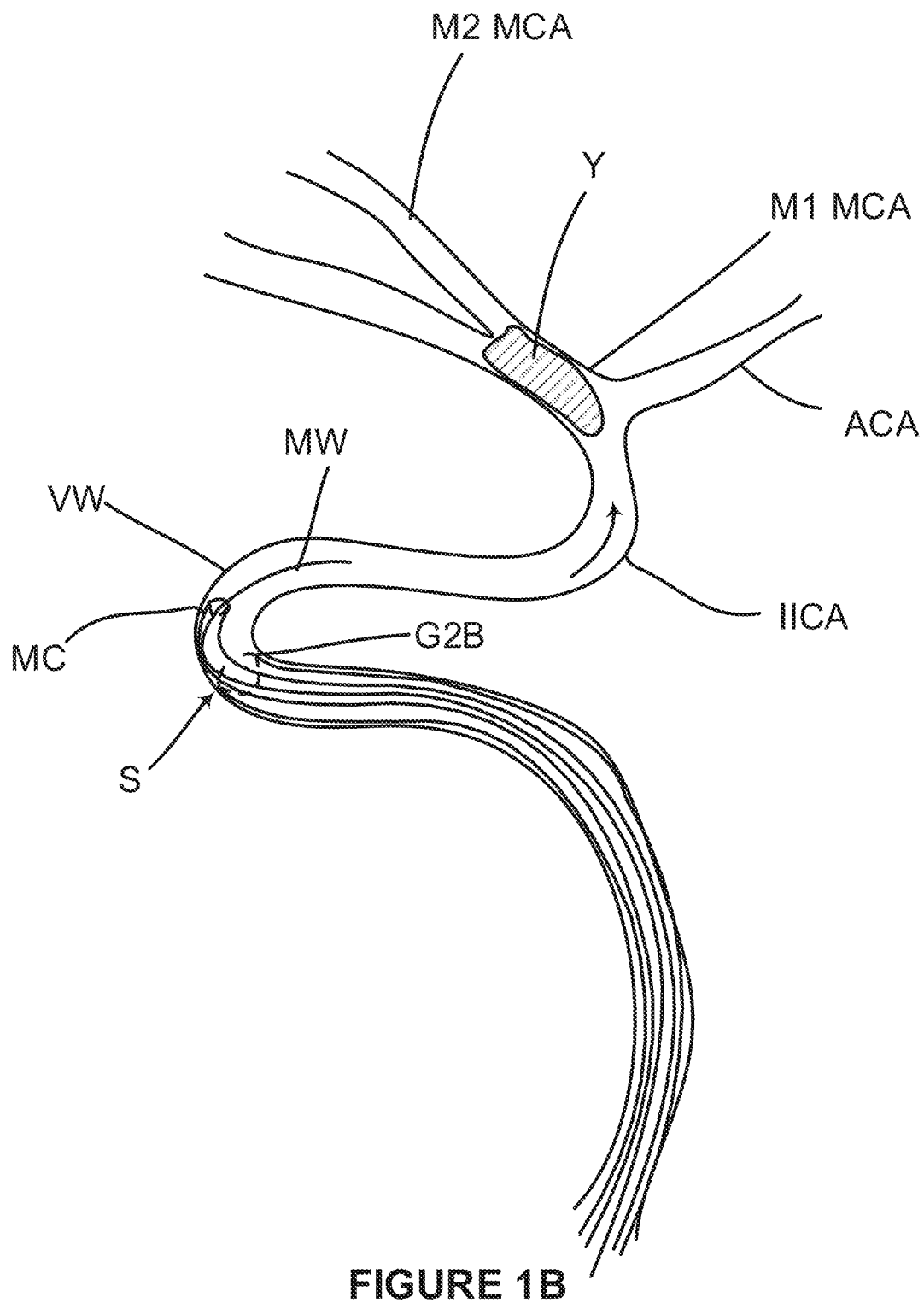
FIGS. 1B to 1G illustrate procedural steps of navigating a G2B/AC catheter through a tortuous section after the G2B/AC catheter has become stuck at S including as the G2B/AC becomes stuck (FIG. 1B), positioning a redirection device (RD) (FIG. 1C), deploying a RD (FIG. 1D), advancing the G2B/AC past the position S (FIG. 1E), re-sheathing the RD (FIG. 1F) and continuing progression of the G2B/AC (FIG. 1G).

The problem being addressed is shown in FIG. 1B, where a surgeon has successfully maneuvered a G2B, MC and MW to the ophthalmic artery and the G2B has become stuck at a position (referenced herein as S) leading into the tortuous section. Typically, a portion of an edge of the distal tip of the G2B will contact the outer curved section of the artery/vessel wall (VW) and will not be able to be pushed around the curve. The MC and MW are shown projecting a short distance from the distal tip of the G2B.

In accordance with the invention, systems and methods to advance a G2B past these areas are described.

Figure 1C:
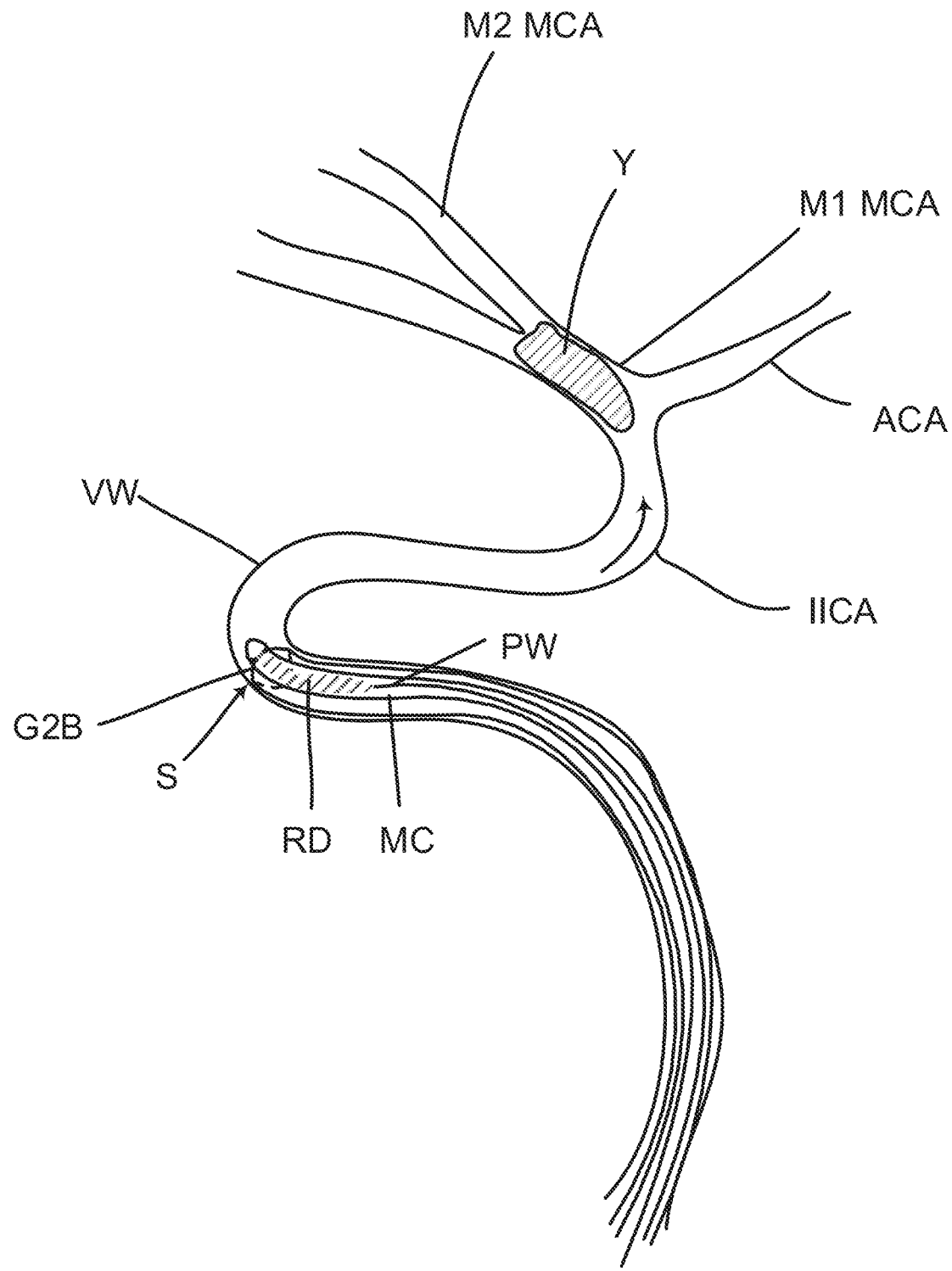

In a first embodiment as shown in FIGS. 1B and 1C, if the G2B becomes stuck, the MC and MW may be withdrawn and a combined assembly of a MC, a redirection device (RD) (retained within a different MC) and push wire PW are advanced to the distal tip of the G2B. For this procedure, the RD is designed to be deployed from the end of the MC simply to assist in moving the G2B around the curve as opposed to a stent designed to engage with and withdraw a clot.

The MC/RD/PW assembly is pre-assembled such that the redirection is frictionally engaged within the MC at the distal tip of the MC. The PW is connected to the proximal end of the RD and can be pushed/pulled relative to the MC such that the RD can be extended from the MC and withdrawn/re-sheathed back into the MC.

The MC/RD/PW assembly is conveyed to the distal tip of the G2B and positioned such that it extends a short distance from the G2B. This distance will typically be between 1-80 mm depending on the ability of the surgeon to navigate this assembly past the G2B. In FIG. 1C this is shown as a relatively short distance of a few mm.

Figure 1D:
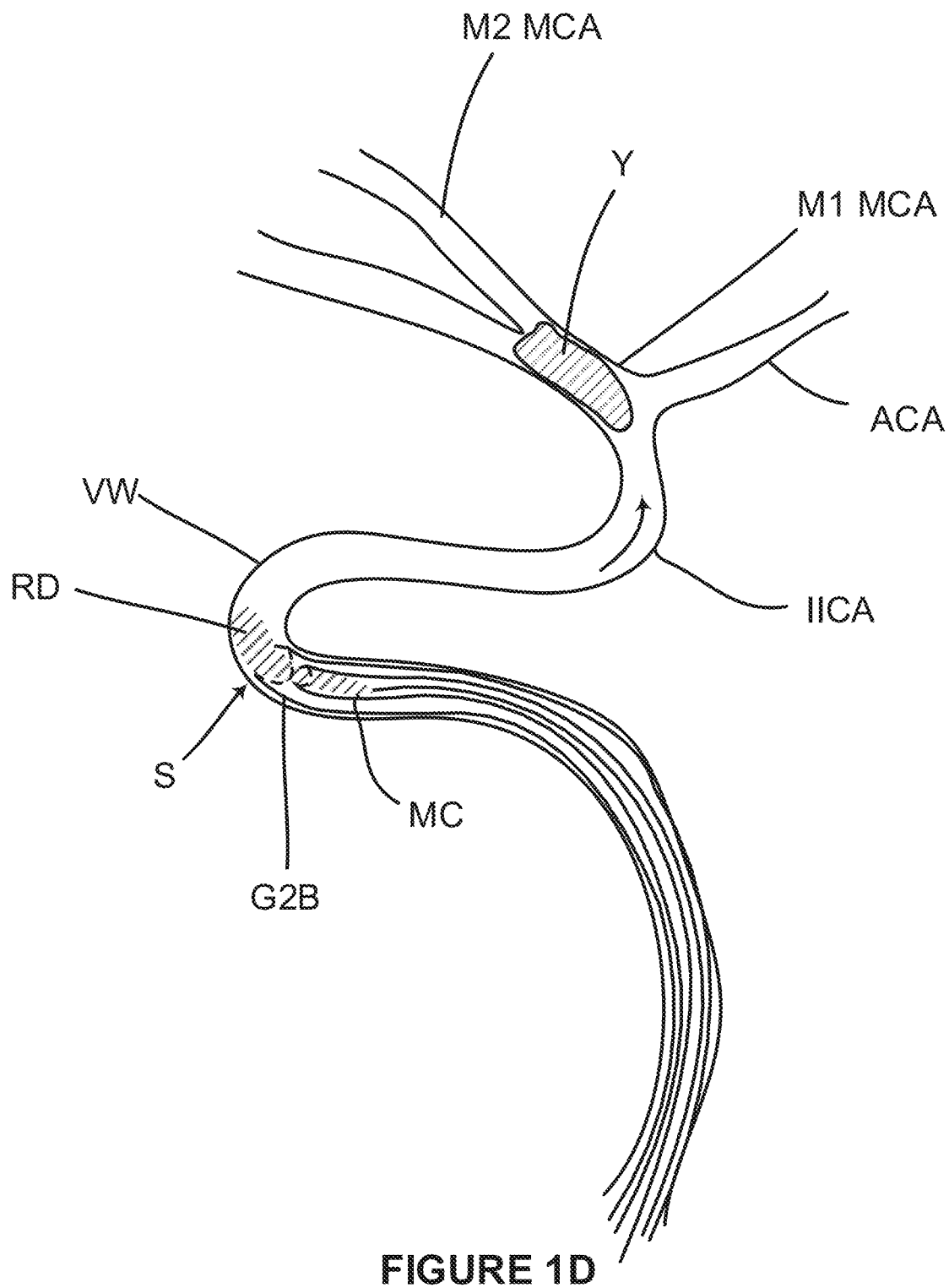

FIG. 1D shows the RD as partially deployed past the G2B. That is, the PW has been held and the MC withdrawn thus partially unsheathing the RD. As shown, the RD is self-expanding and will thus expand to engage with the vessel wall VW as well as the distal tip of the G2B. This expansion and engagement with the G2B will have a tendency to ease the portion of the distal tip of the G2B away from VW at S thus relieving pressure that has caused the G2B to become stuck.

Figure 1E:
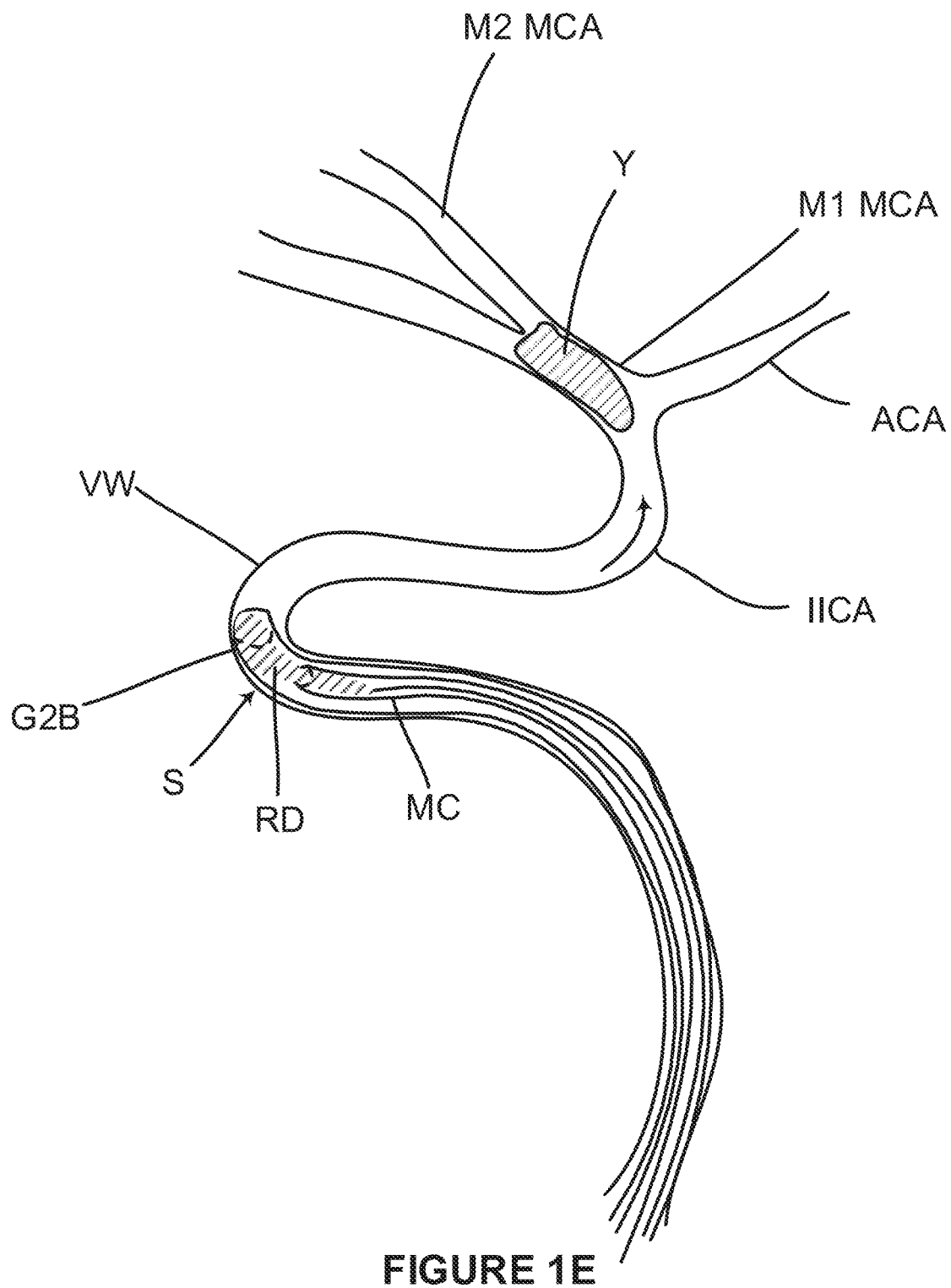
Figure 1F:
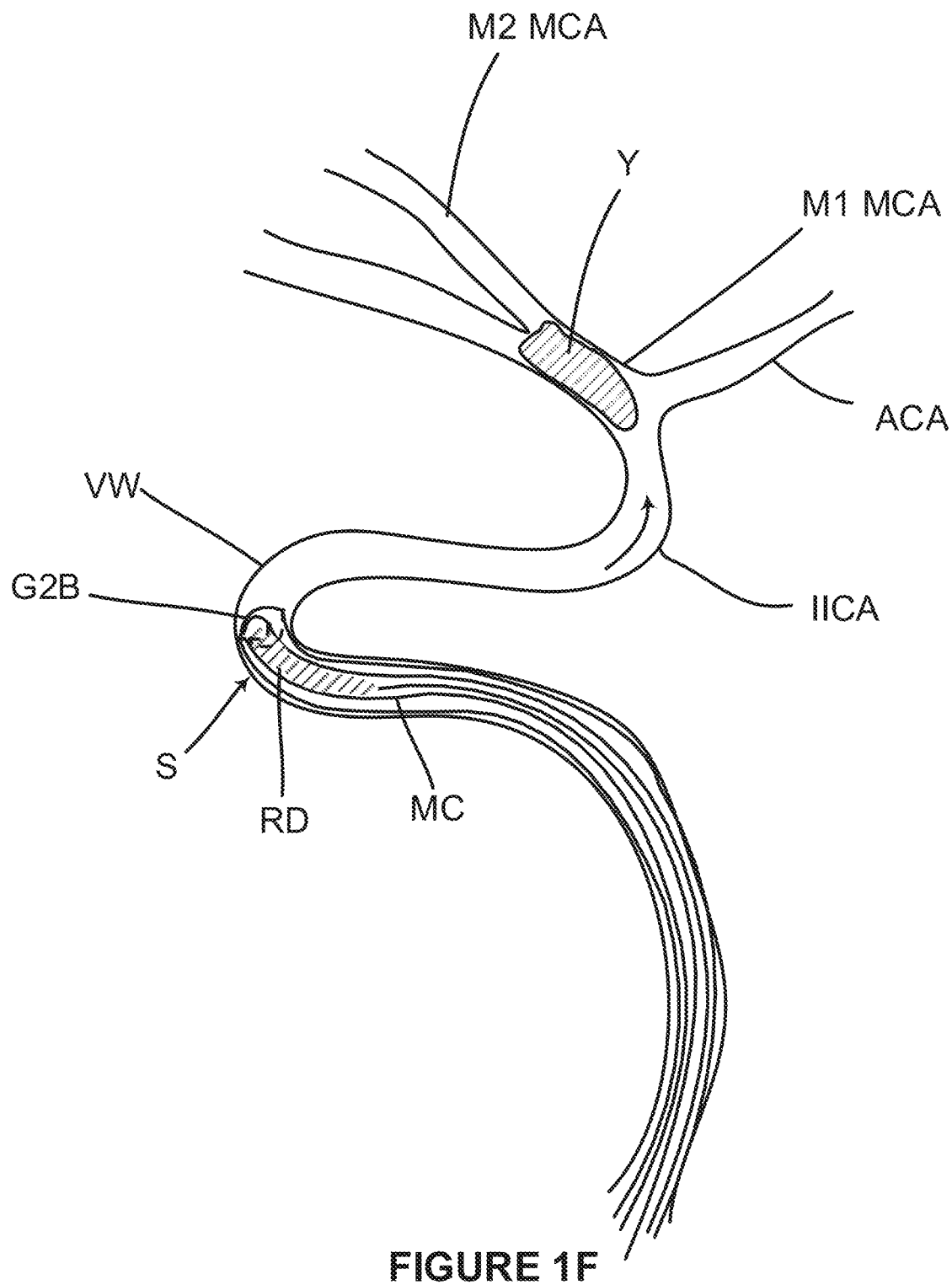
Figure 1G:
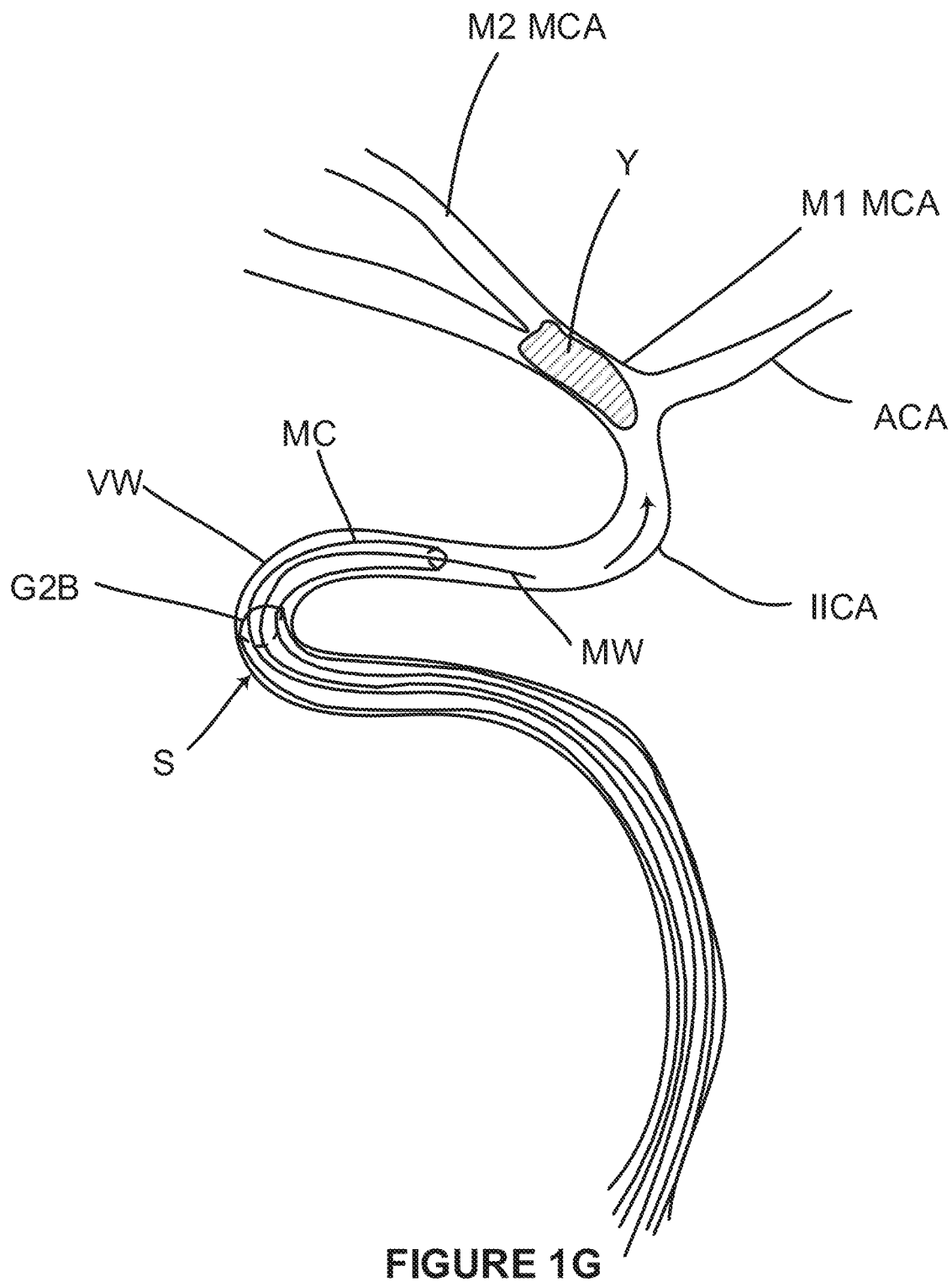

As the pressure is released, as shown in FIG. 1E, the G2B can be pushed forward over the RD thus allowing the G2B to be advanced past S. The RD can then be re-sheathed as shown in FIG. 1F by pushing the MC forward. The MC/RD/PW assembly can then be withdrawn and the MC/MW re-introduced to continue advancement of the G2B to the clot Y as shown in FIG. 1G.

The entire process can be repeated as necessary should the G2B become stuck again.

Figure 2A:
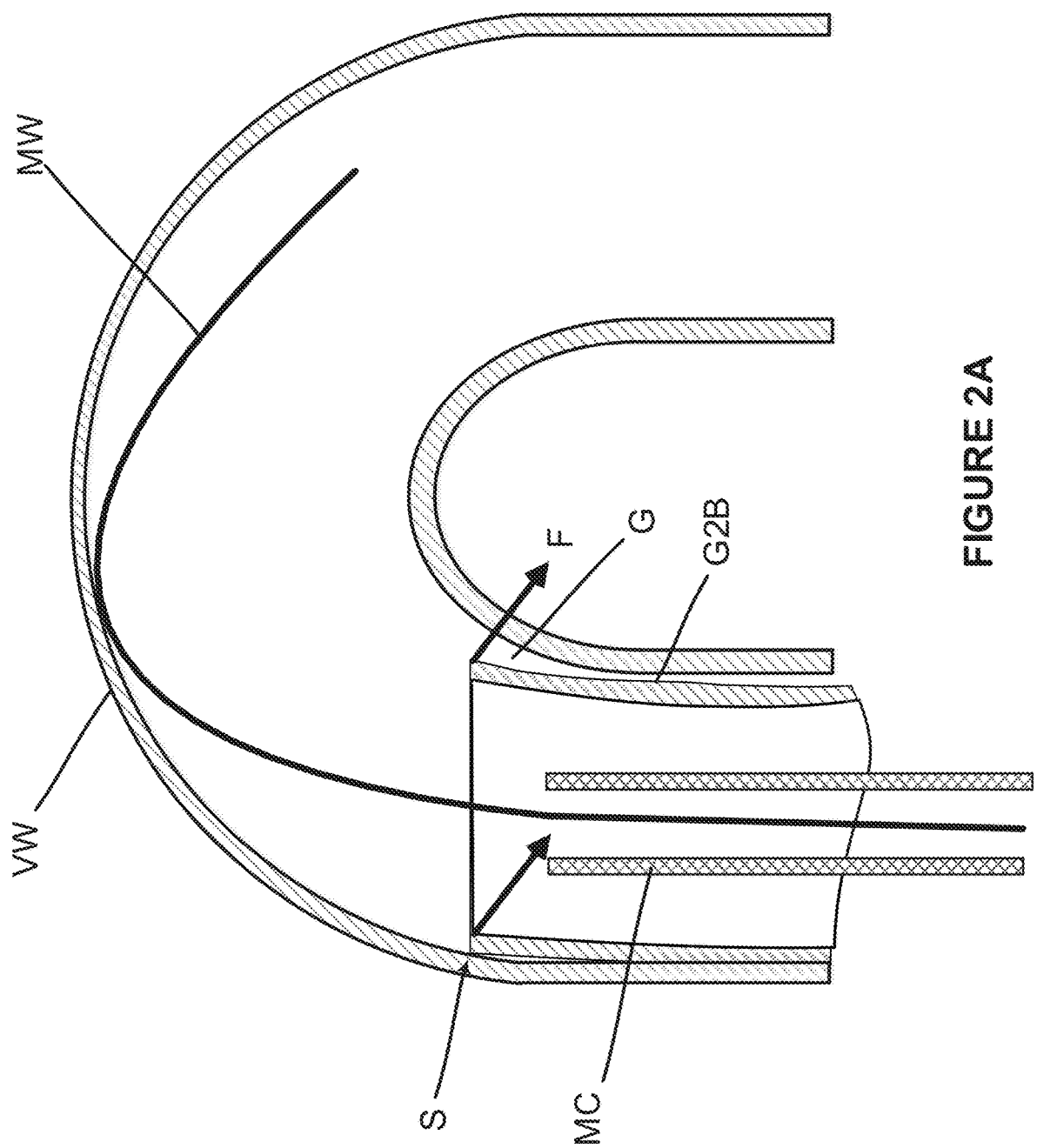
FIGS. 2A, 2B and 2C are side and cross-sectional sketches showing details of a process by which pressure is relieved during advancement of a G2B/AC.
Figure 2B:
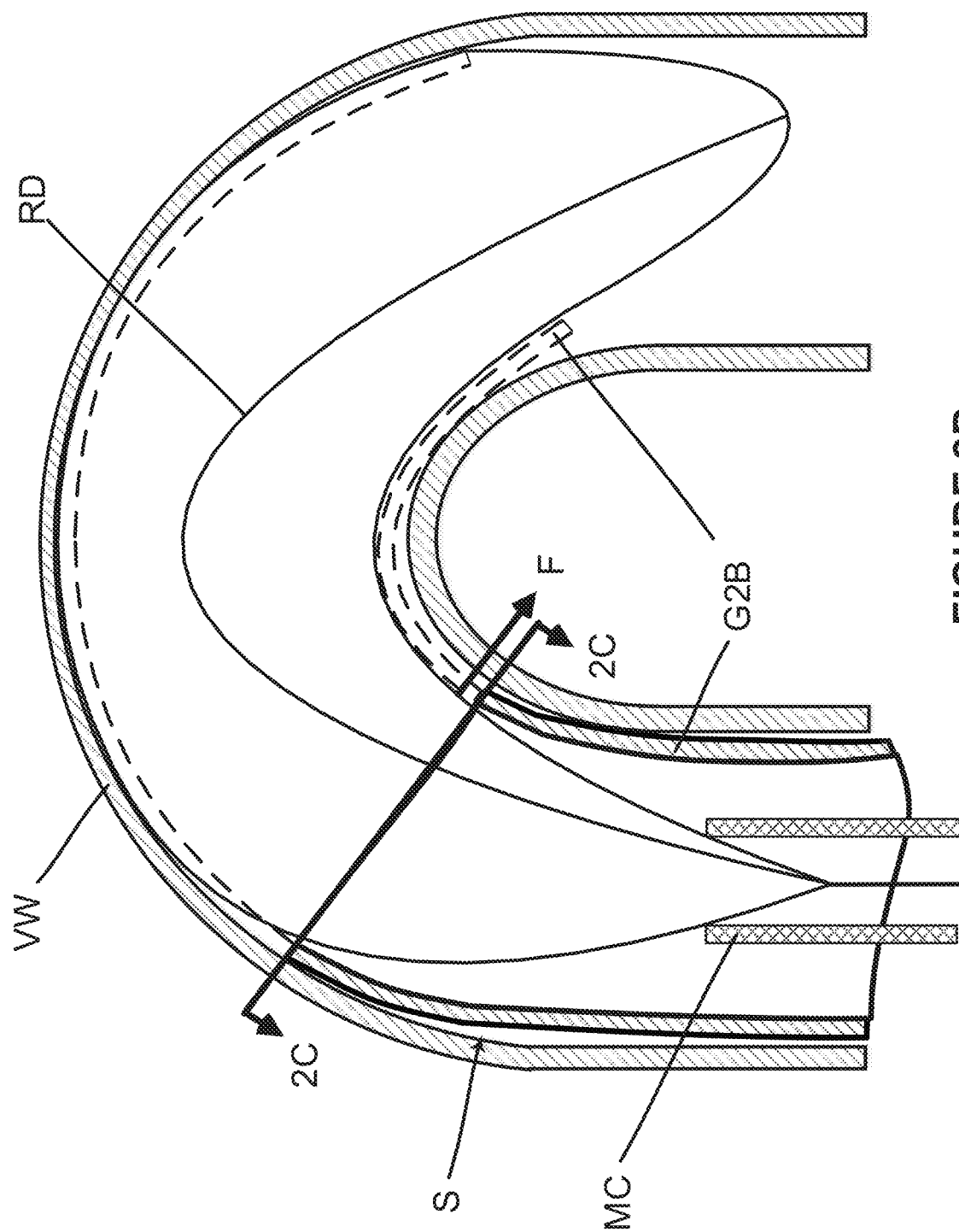
Figure 2C:
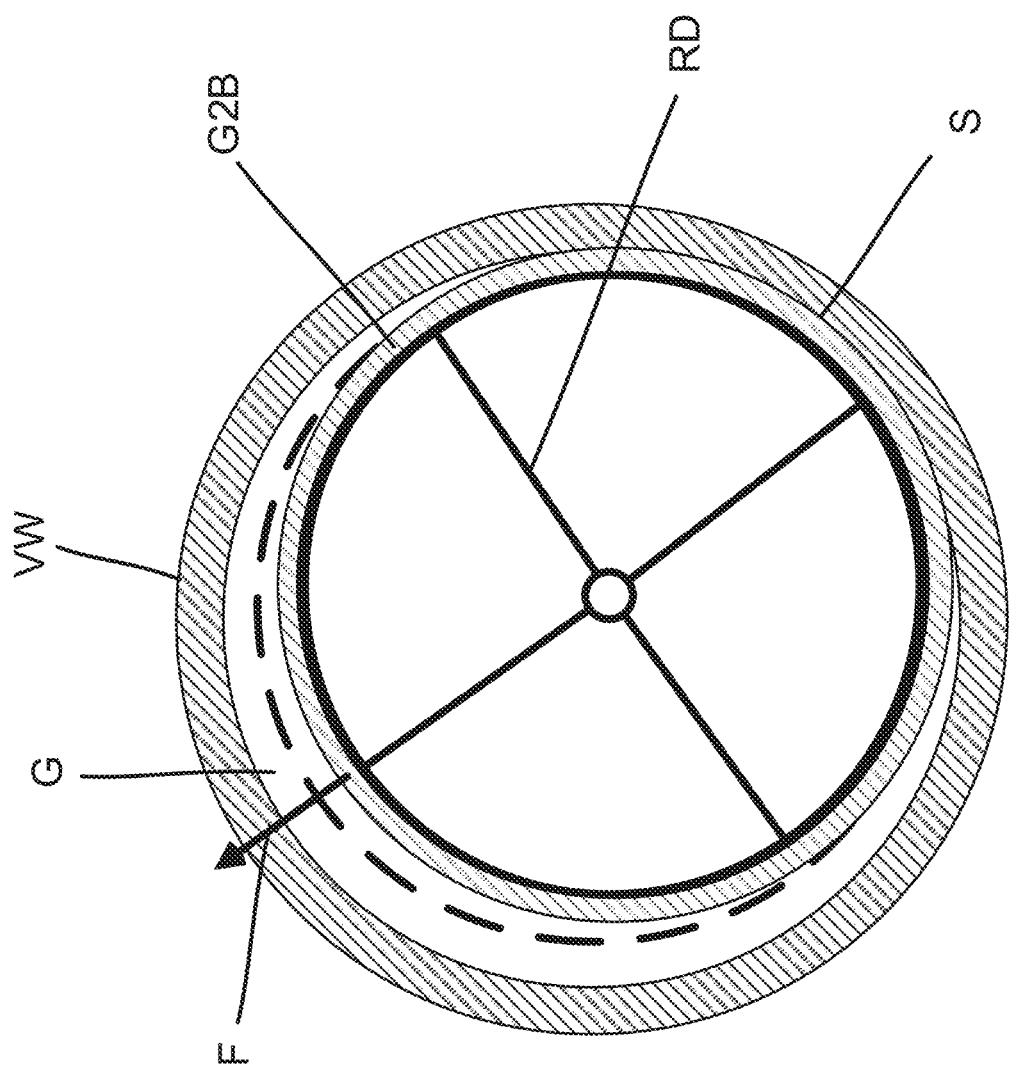

Further details of a typical process are shown in FIGS. 2A, 2B and 2C in a curved section of a patient's vasculature.

As shown in FIG. 2A, an edge of the G2B has come into contact with an outer surface of the VW preventing further progress. In this scenario, a small gap G may exist between an inner surface of the VW and the G2B. The MC is shown near the distal tip of the G2B and the MW is shown progressing around the tortuous section of the vasculature.

FIG. 2B shows a mechanism by which the RD may cause deflection of the distal tip of the G2B after it has been deployed from the MC and G2B. As shown, the RD (note: any cross-wires of the RD have been excluded for clarity) has been deployed such that it extends around the curve of the tortuous section wherein the self-expanding wires of the RD have deflected the tip of the G2B in a direction F against the inner surface of the vessel thus eliminating the gap G and relieving pressure at S. With the pressure relieved, the G2B can be advanced past S over the RD. Ideally, to the extent that the deployed RD prevents the G2B from getting stuck again, the G2B may in some situations be advanced over the RD to a position as shown by the dotted lines in FIG. 2B.

FIG. 2C shows a schematic cross-section of the distal tip of a G2B at line 2C-2C and how the RD (note: any cross wires also not shown for clarity) may deflect the G2B to relieve pressure at S and move the G2B to fill gap G. The dotted lines show the G2B after it has been deflected.

FIGS. 3A-3F show the deployment of a RD in accordance with an alternate embodiment where the MW, RD and MC are designed to enable simultaneous advancement of a G2B, MW, MC and RD thus enabling fewer steps in the event that the G2B becomes stuck. Moreover, in one embodiment, as discussed below the need for a MC may also be obviated.

FIGS. 3A-3F are drawn for clarity as a projection of a curved section of the vasculature onto a flat surface (see inset of FIG. 3A) and, as such, are intended to show the sequence of steps showing the progression of the components of the system through curved sections of the vasculature and the manipulation of the different components relative to one another.

Figure 3A:
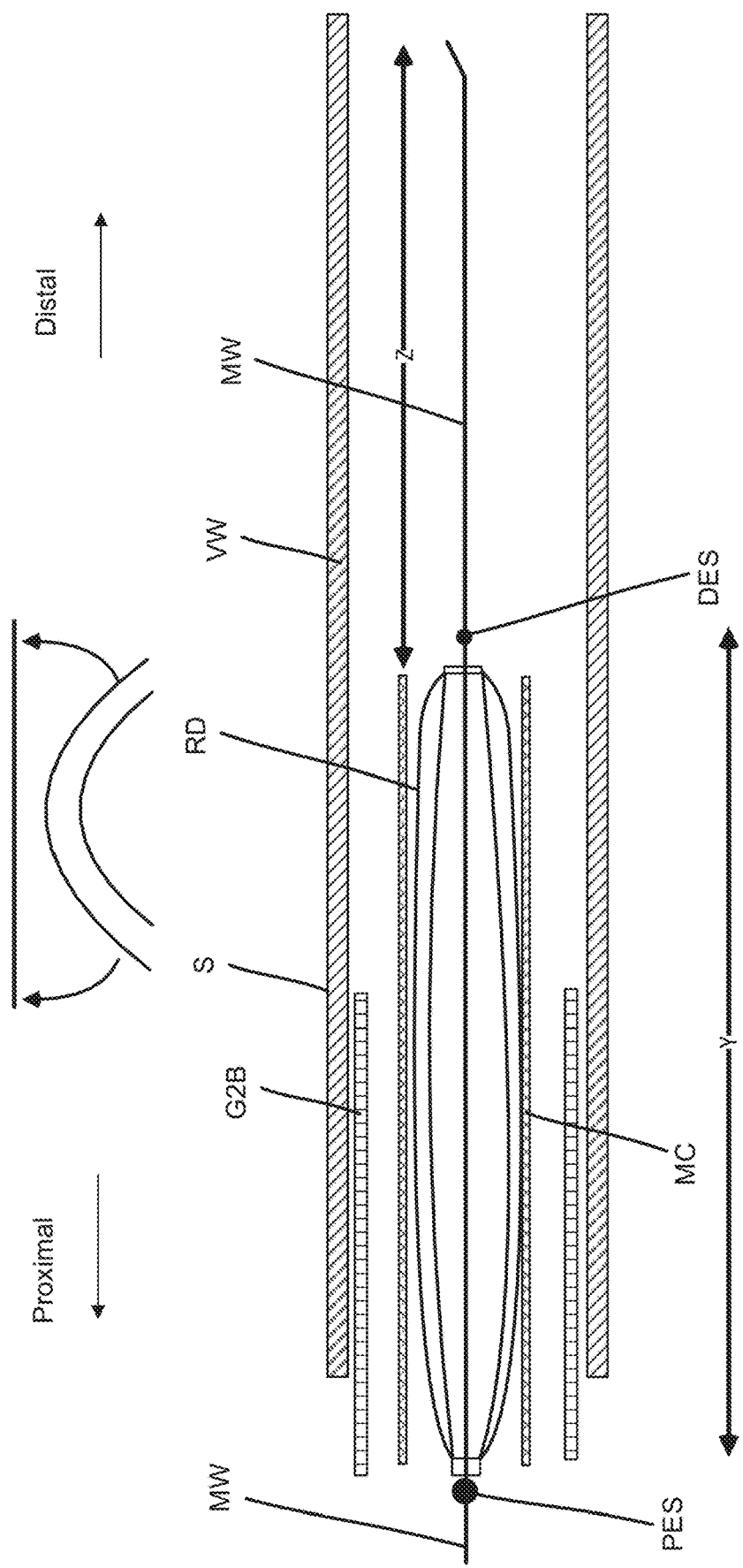
FIGS. 3A-3F are sketches showing the process of advancing a G2B/AC utilizing a RD in accordance with one embodiment of the invention.

In the embodiment shown in FIG. 3A, a G2B is shown stuck at S. A RD is operatively retained/compressed within a MC and a MW capable of linear movement relative to the RD between two positions is retained within the MS and MC.

In this embodiment, the MW includes a distal end stop (DES) and proximal end stop (PES) that can operatively engage with a proximal end of the RD to both "push" the MS from the MC and "pull" the RD into the MC. The DES and PES may be positioned approximately 10 cm from one another along the length of the MW and thus enable the MW to move co-axially a distance of Y (eg. 10 cm) without engagement with the RD. The DES may be positioned a distance Z (eg. 6-10 cm) from the distal tip of the MW.

Accordingly, the surgeon may advance the combined G2B, MW, MC and RD components simultaneously wherein during advancement, the RD is frictionally retained at the distal end of the MC and the MW can be steered and advanced by pushing the MW forward up to the distance Y and then the MC and G2B can be progressively pushed forward over the MW.

Figure 3B:
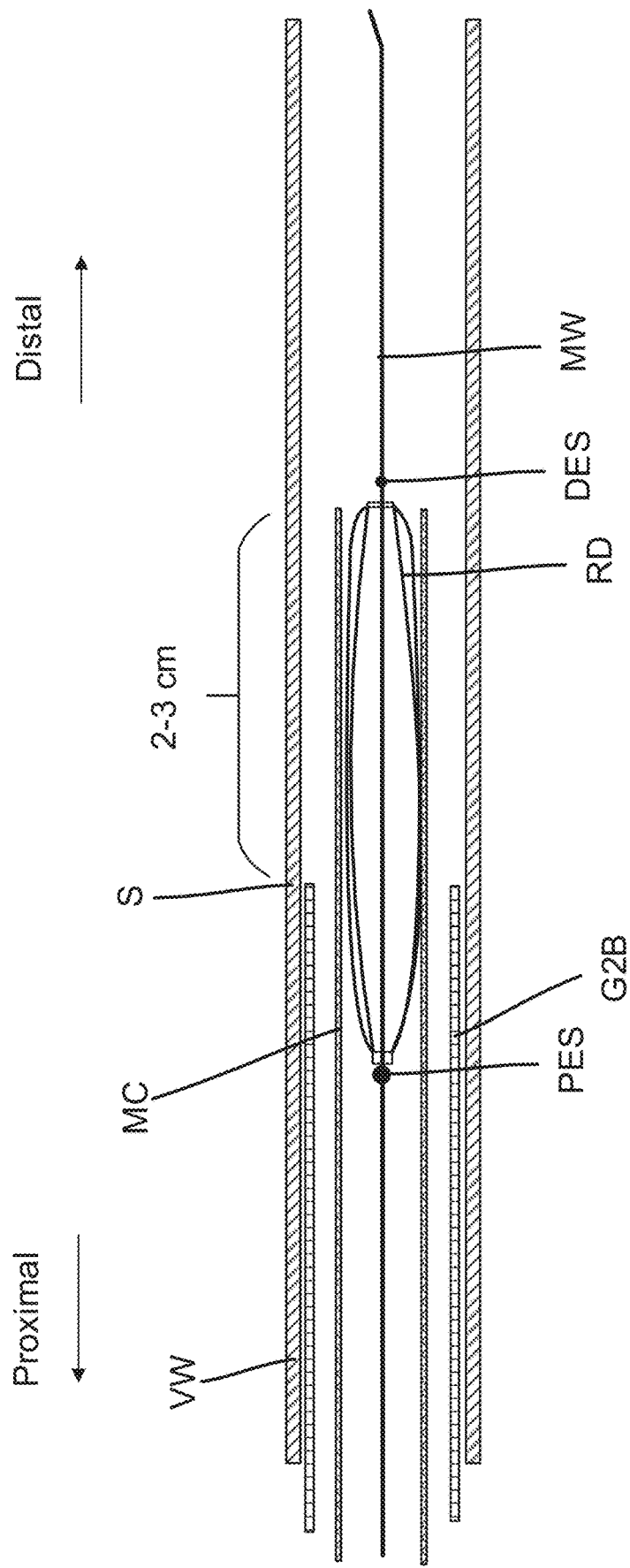
Figure 3C:
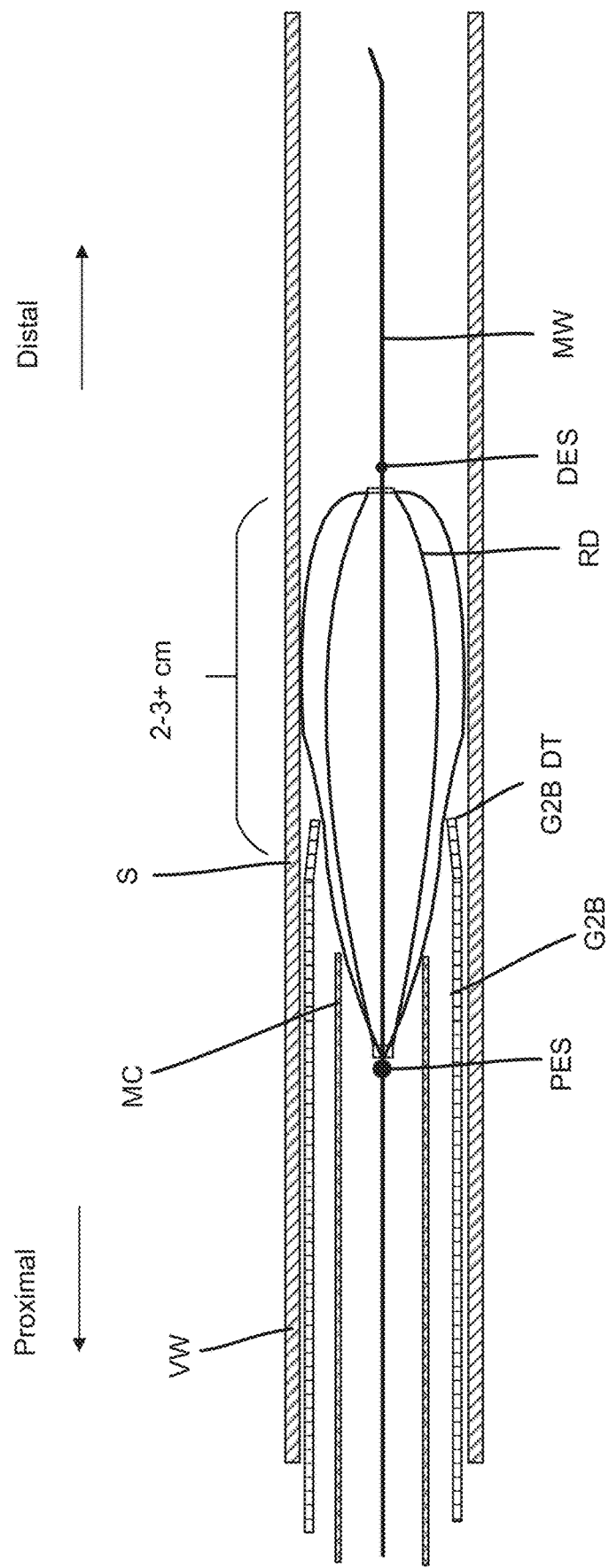
Figure 3D:
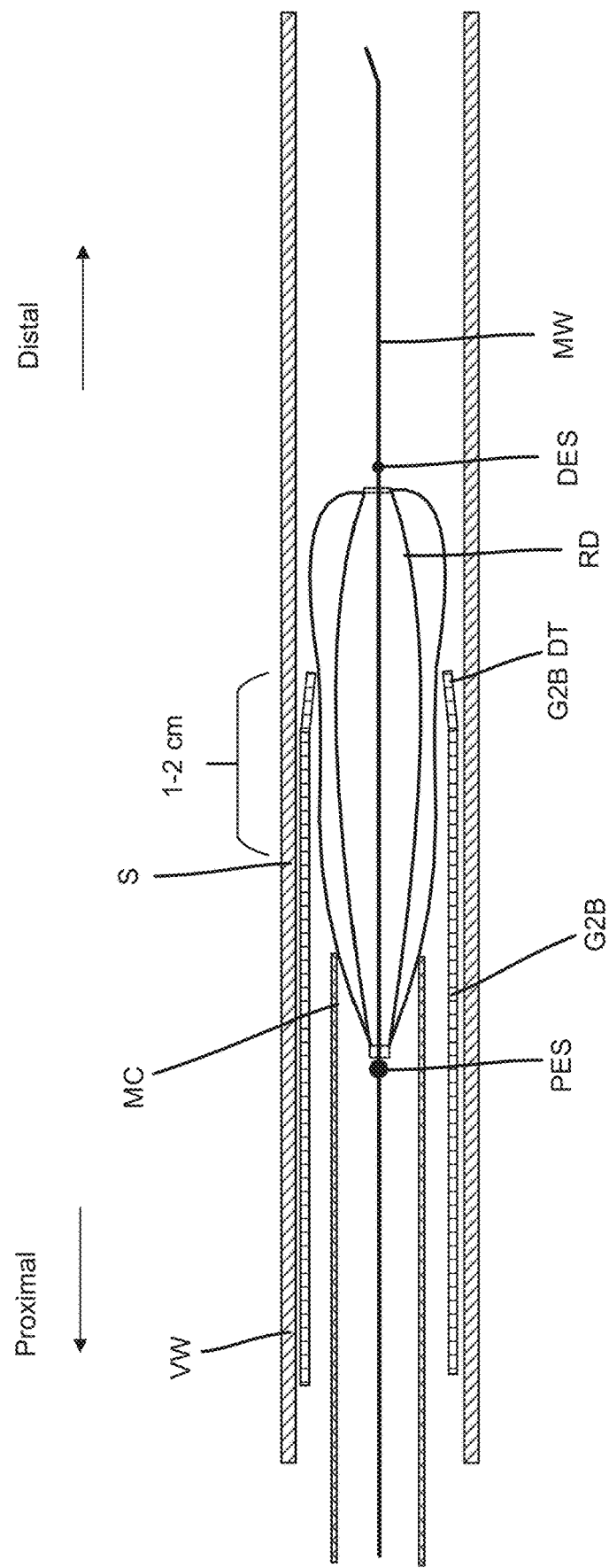
Figure 3E:
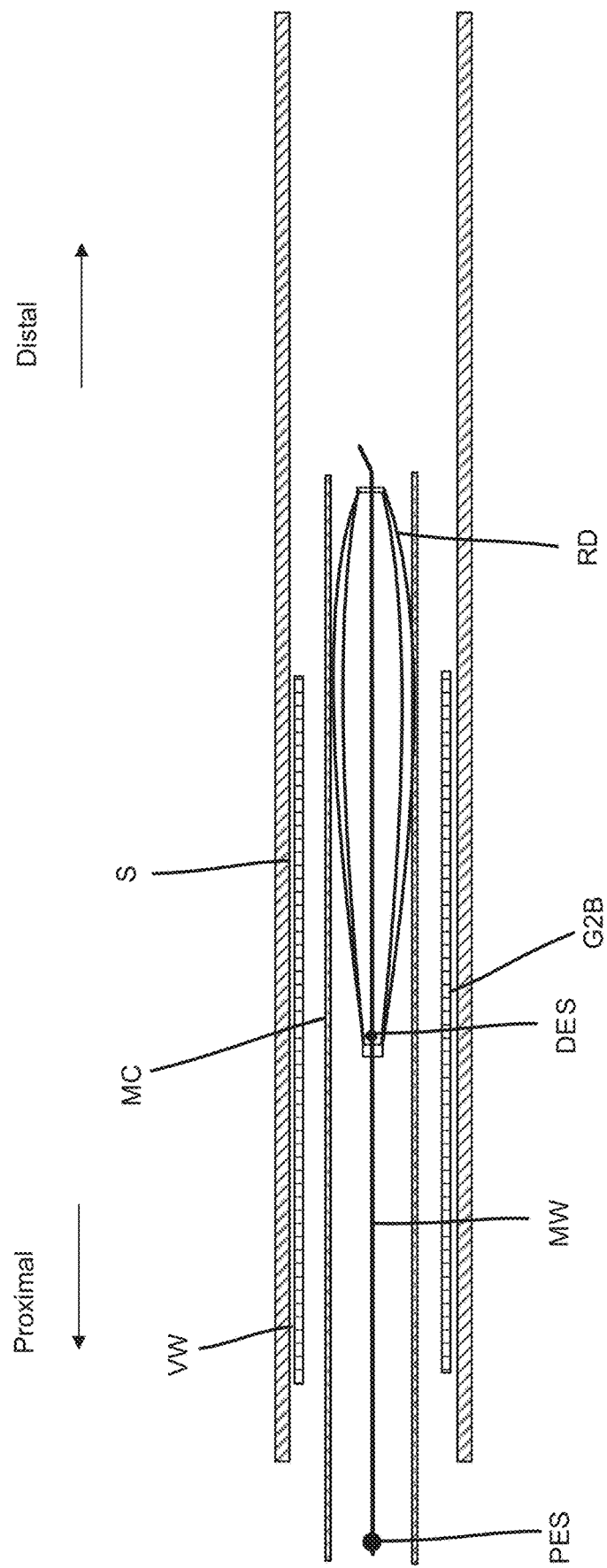

In the event that the G2B gets stuck as shown in FIGS. 3A and 3B, the PES of the MW may be used to hold the RD at a position forward of the G2B. As shown in FIG. 3B, after the G2B has become stuck, the MC/RD may be moved forward to a desired position forward of S (shown illustratively as 2-3 cm). The MW PES is positioned proximal to the MS and the MC is withdrawn (FIG. 3C). As shown schematically in FIG. 3C, as the RD is deployed and engages with the distal tip of the G2B, this may relieve pressure on the distal tip and allow the G2B to be pushed forward and ride over the RD (FIG. 3D).

The RD may then be re-sheathed by moving the MW proximally such that the DES engages with the proximal end of the RD thus holding the MS in position. The RD can be re-sheathed by either pushing the MC forward (FIG. 3E) or pulling the MW proximally.

Figure 3F:
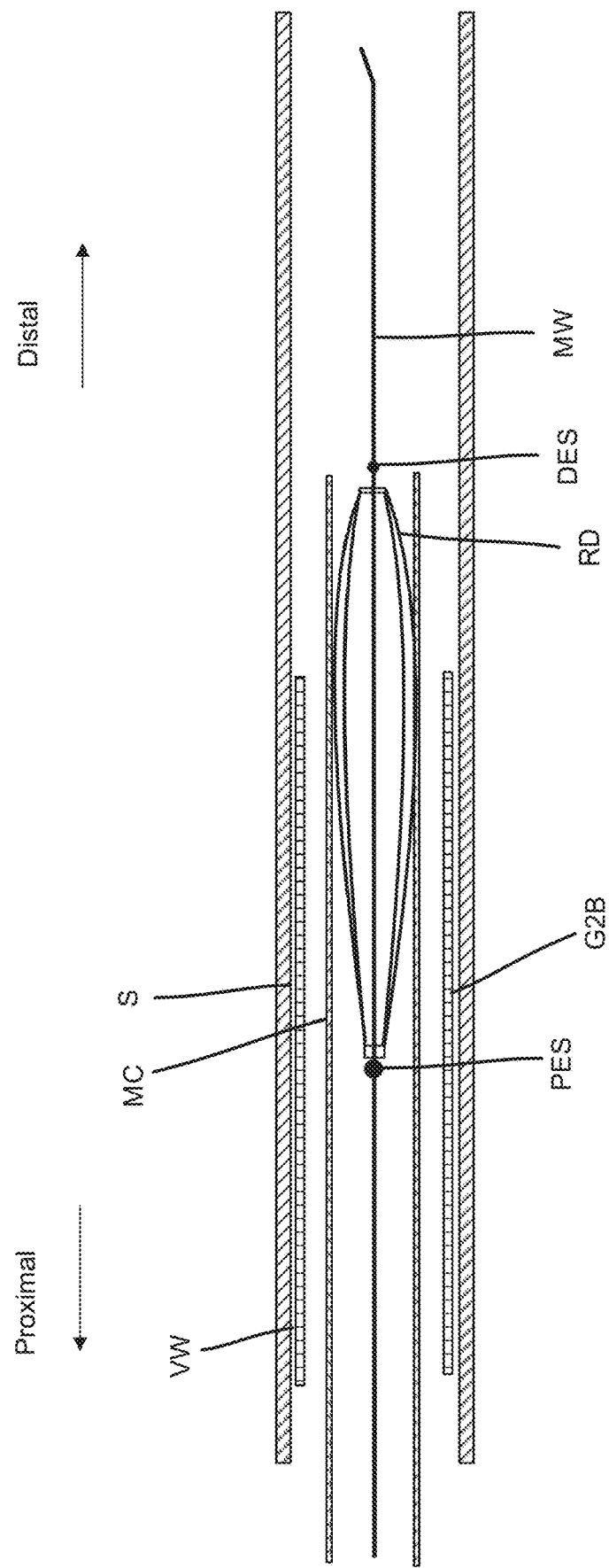

When the RD has been re-sheathed, the assembly may be continued to be advanced as shown in FIG. 3F.

Other Embodiments

Controlled Expansion Redirection Device

Figure 4A:
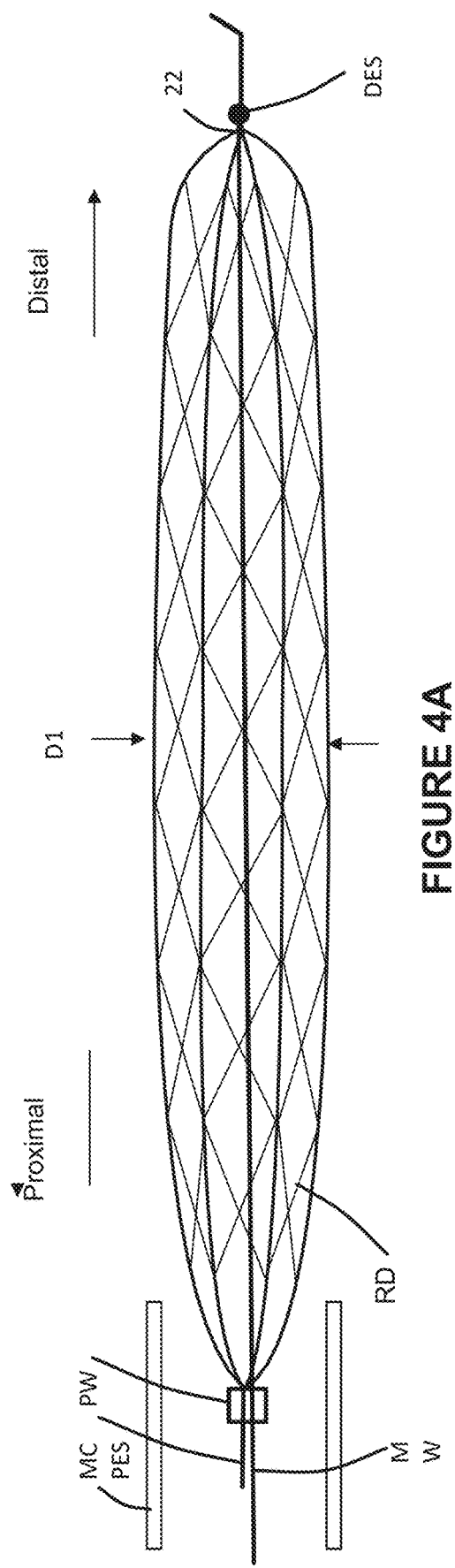
FIGS. 4A and 4B are sketches showing a manually expandable and compressible RD in accordance with one embodiment of the invention.
Figure 4B:
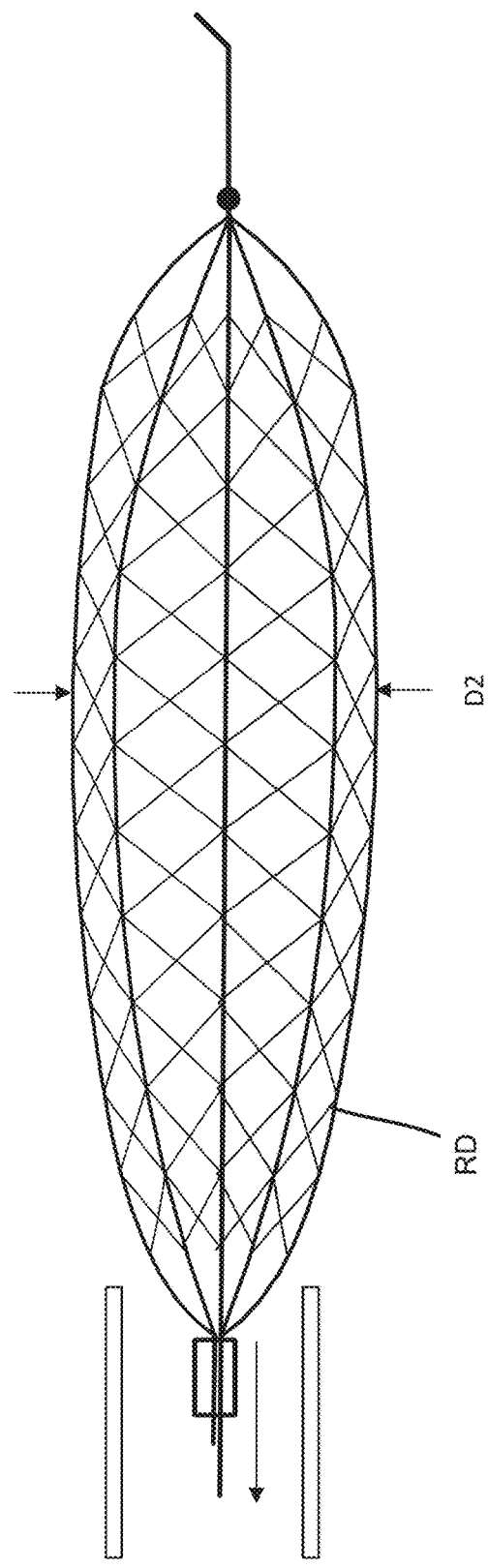

In another embodiment, as shown in FIGS. 4A and 4B, the RD may be non-self-expanding stent, that is, a stent that can be manually manipulated/locked between a collapsed (4A) and expanded (4B) configuration thus giving the surgeon additional control on the application of RD pressure to assist in relieving pressure at S.

As shown in FIGS. 4A and 4B, the RD includes a wire mesh having a push wire PW fixed to the proximal end 20 of the RD and a MW fixed to the distal end 22 of the MS. In this embodiment, movement of the PW relative to the MW causes a shortening or lengthening of the distance between the proximal and distal ends of the RD and corresponding expansion or contraction respectively of the diameter D of the MS. That is, in FIG. 4B, the PW has been held and the MW pulled proximally so as cause D to expand. The PW and MW may be retained within a PES and MC to ensure coordinated movement and include appropriate external locking/positioning mechanisms (not shown) to limit/control the relative movement and positioning of MW and PW relative to one another.

The MW may also be provided with a DES distal and external to the RD that allows for forward movement of the MW relative to the RD so as to enable the MW to be advanced and steered/torqued in the manner as described above.

Deployment without a MC

In another embodiment, the RD is conveyed distally within the G2B without a MC. The embodiment of FIGS. 4A and 4B is particularly suited for this method in that the stiffness of the RD can be controlled during advancement. That is, if the MS is being conveyed forward and the MW and PW are positioned in a mid-setting, if the surgeon determines that the system needs to be less stiff, the RD can be lengthened to reduce the stiffness. Similarly, additional stiffness can be introduced by shortening the DES to PES distance.

Deployment at Bifurcation

Figure 5A:
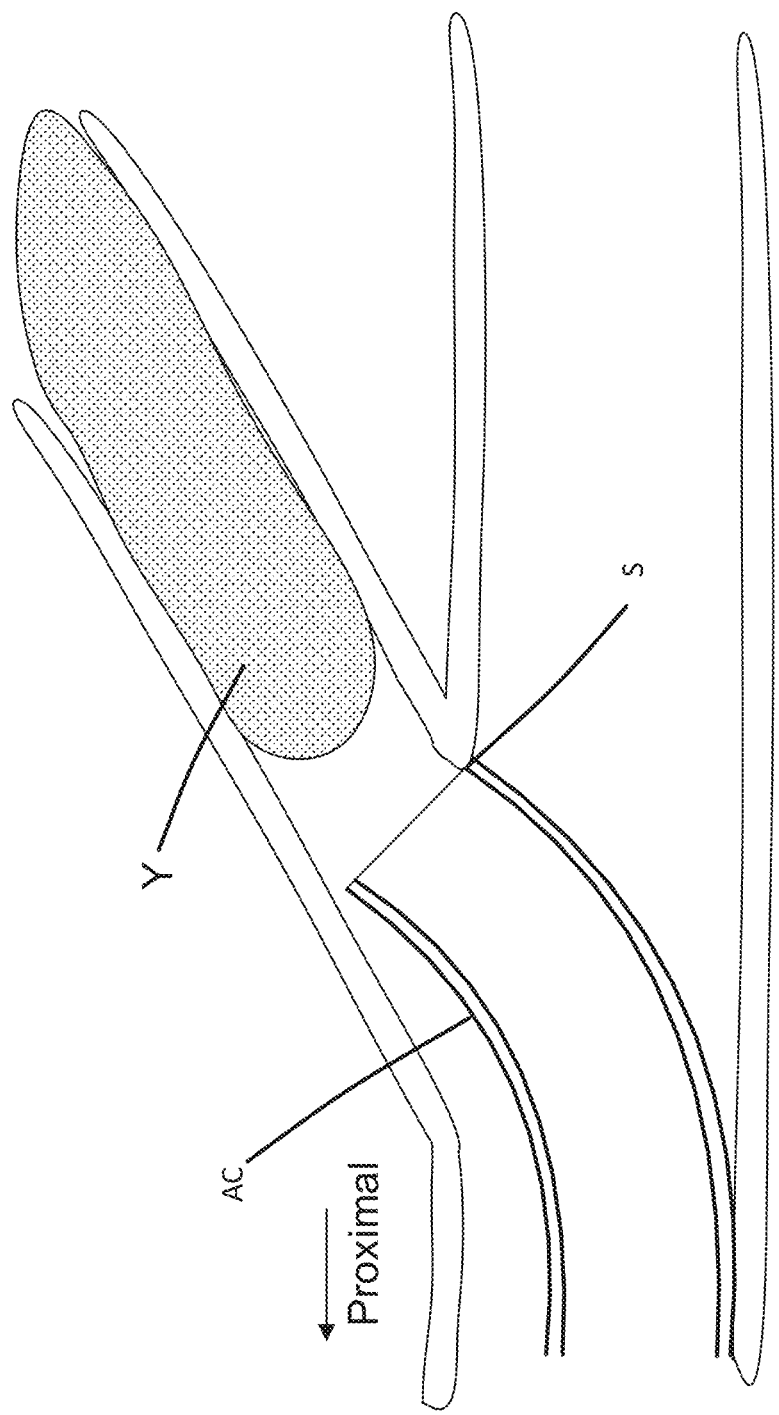
FIGS. 5A-5D are sketches showing the deployment of an RD at a vessel bifurcation where a clot is located partially within one arm.
Figure 5B:
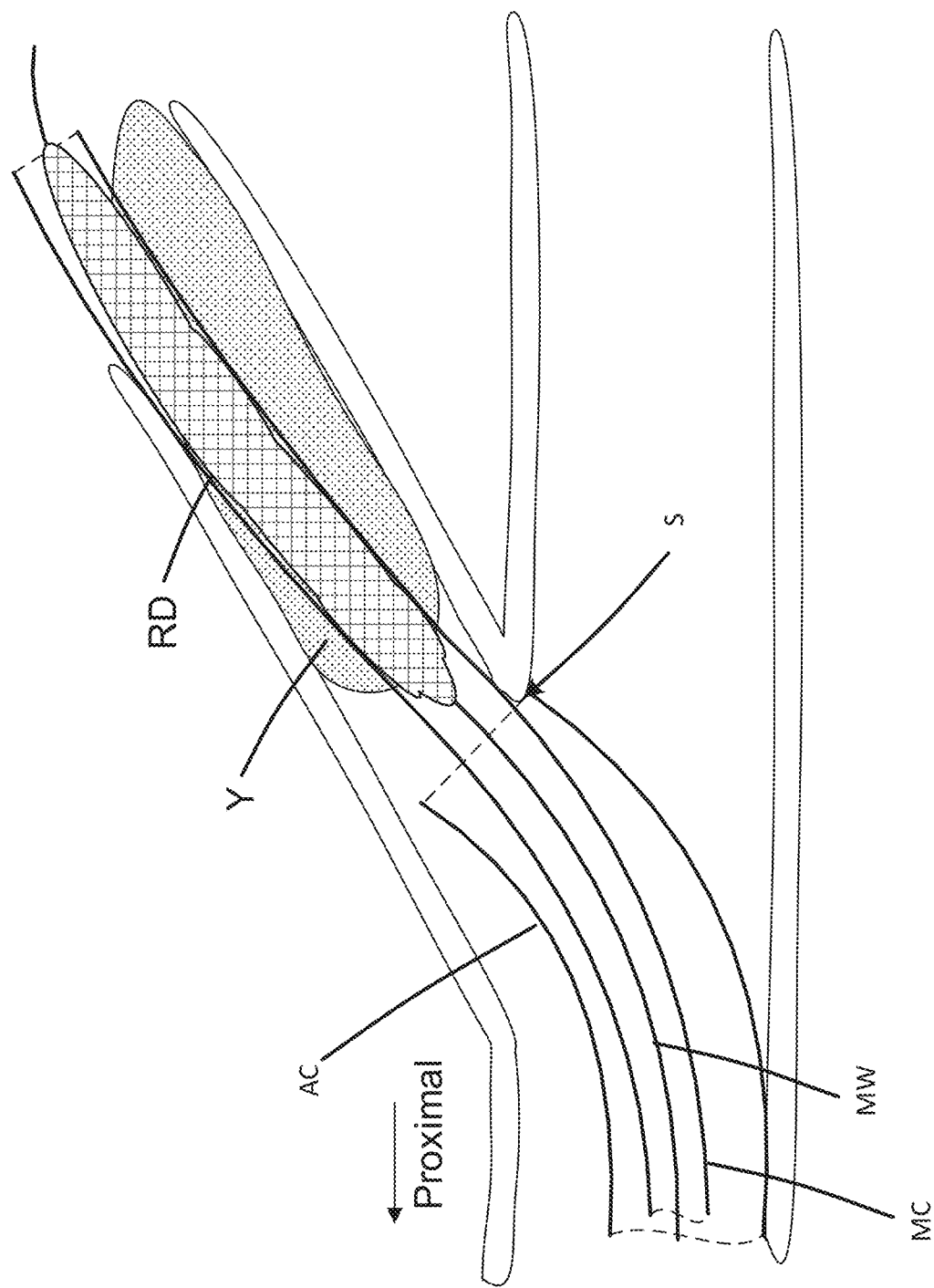
Figure 5C:
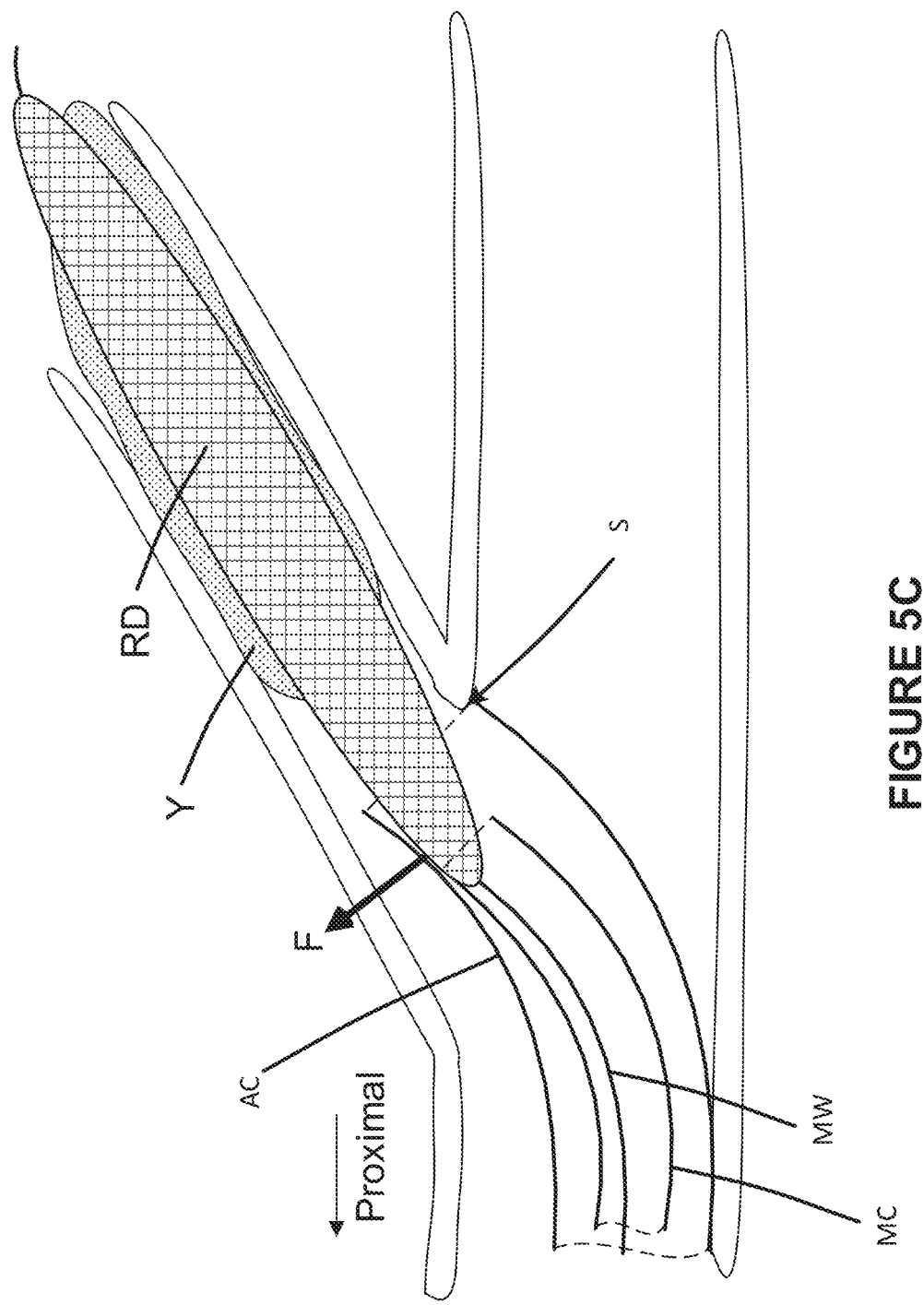
Figure 5D:
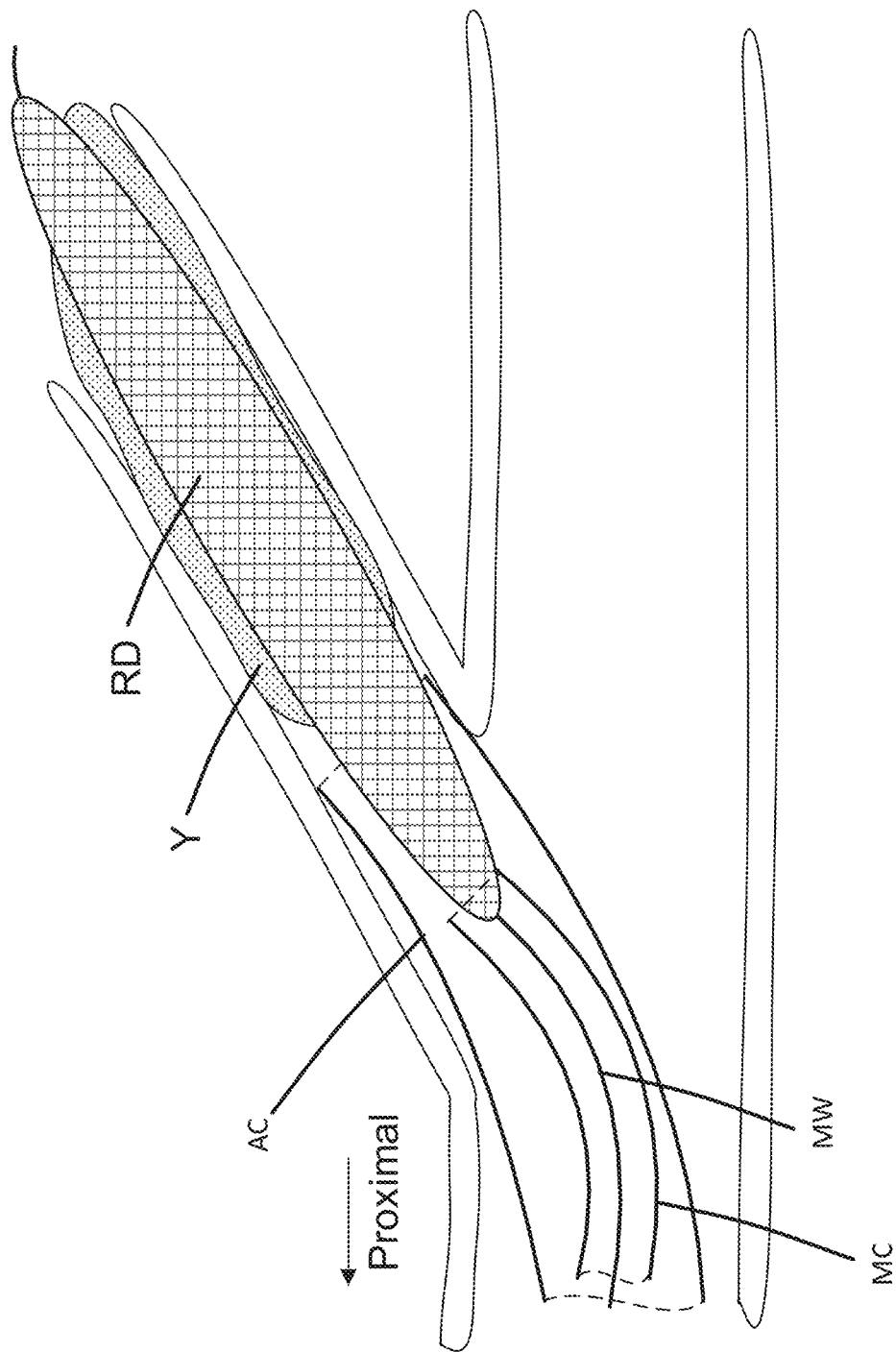

FIGS. 5A-5D illustrate deployment of a redirection device RD at a vessel bifurcation where the RD can function both as a RD and clot retrieval system. As shown in FIG. 5A, a clot Y is located at a bifurcation of a vessel with the proximal face of the clot just beyond the bifurcation. An aspiration catheter such as a AC/G2B has been positioned close and proximal to the proximal end of the clot by the manipulation of MWs and MCs as is known but has become stuck where proximal edge of the AC has hit the edge of the bifurcation at S. As it is desirable to advance the AC closer to the proximal edge of the clot, an RD is deployed as shown in FIGS. 5B-5D to advance the AC closer.

The procedural steps shown in FIGS. 5A-5D are loosely similar (but with key differences) to steps of deploying a stent retriever at a clot. That is, in the past, in one technique a MW is steered to the proximal face of the clot and pushed through the clot. A MC containing a stent retriever, is pushed over the MW and through the clot such that the distal tip of the MC is beyond the clot. The MC is then withdrawn such that the stent retriever is deployed within the clot where, after a short time to allow the clot to engage with the stent retriever, both the stent retriever and MC can be withdrawn into an aspiration catheter that may be some distance upstream.

FIG. 5B shows a MC containing an RD that has been positioned as described above. Although not shown in this figure, the RD generally has a greater proportion of longitudinal wires to enable engagement with the clot.

FIG. 5C shows the MC having been withdrawn to allow the RD to expand and engage with the clot. In this figure, the MC and RD have been positioned such that the proximal end of the RD is within the AC. As described above, regardless if the RD is self-expanding or manually-expandable, the RD, AC and MC are positioned/manipulated in order to exert a force F on the distal tip of the AC to cause it to be redirected away from the bifurcation edge.

As shown in FIG. 5D, after the distal edge of the AC has been redirected, the AC can be pushed forward over the RD such that the distal edge of the AC is adjacent the proximal edge of the clot. By pulling back on the RD in combination with suction applied through the AC, the clot can be removed.

Although the present invention has been described and illustrated with respect to preferred embodiments and preferred uses thereof, it is not to be so limited since modifications and changes can be made therein which are within the full, intended scope of the invention as understood by those skilled in the art.

The invention claimed is:

1. A method for advancing an aspiration catheter (AC) through a tortuous section of a cerebral artery, particularly when the AC has become stuck within the tortuous section, the method comprising the steps of:
   a) conveying a redirection device (RD) operatively retained within a microcatheter (MC) through the AC to a distal tip of the AC, the RD having a push wire (PW) operatively connected to a proximal end of the RD wherein the RD is expandable relative to the size of the MC;
   b) conveying the MC and RD to a position beyond the distal tip of the AC;
   c) withdrawing the MC relative to the RD to cause a distal tip of the RD to emerge from the MC and expand to engage with an inner wall of the cerebral artery and the distal tip of the AC and wherein contact of the RD with both the cerebral artery and AC relieves pressure on the distal tip of the AC preventing forward movement of the AC; and,
   d) when pressure has been relieved and/or the AC has been re-aligned with the cerebral artery, advancing the AC forward over the RD.

2. The method as in claim 1 further comprising the steps of:
   a) re-sheathing the RD within the MC; and,
   b) withdrawing the RD and MC from the AC.

3. The method as in claim 2 further comprising the step of:
   a) advancing a MC operatively containing a microwire (MW) within the AC to provide support to the AC for further advancement of the AC within the cerebral artery.

4. A method for advancing an aspiration catheter (AC) through a tortuous section of a cerebral artery, particularly when the AC has become stuck within the tortuous section, the method comprising the steps of:
   a) conveying a redirection device (RD) operatively retained within the AC to a distal tip of the AC, the RD having a push wire (PW) operatively connected to a proximal end of the RD wherein the RD is expandable relative to the size of the AC;
   b) pushing the RD to a position beyond the distal tip of the AC so as to cause a distal tip of the RD to emerge from the AC and expand to engage with an inner wall of the cerebral artery and the distal tip of the AC and wherein contact of the RD with both the cerebral artery and AC relieves pressure on the distal tip of the AC preventing forward move of the AC; and,
   c) when pressure has been relieved and/or when the AC has been re-aligned within the cerebral artery, advancing the AC forward over the RD.

5. A system for relieving pressure and re-aligning an aspiration catheter (AC) in contact with a cerebral artery, particularly within a tortuous section of the cerebral artery comprising: a redirection device (RD) operatively contained within a microcatheter (MC), the RD expandable and having a microwire (MW) operatively connected to a proximal end of the RD wherein the RD is deployable and re-sheathable from a distal tip of the MC and wherein upon deployment the RD is expandable to engage with an inner wall of the cerebral artery and a distal tip of the AC to relieve contact pressure between the AC and cerebral artery and/or re-align the AC within the cerebral artery.

6. The system as in claim 5 where the RD is self-expanding.

7. The system as in claim 5 where the RD is manually expandable and compressible.

8. The system as in claim 7 where the system includes a first MW fixed to a proximal end of the RD and a second MW fixed to a distal end of the RD, the second MW being telescopically retained within the RD and where movement of the first MW relative to the second MW causes shortening or lengthening of the RD to cause expansion and compression of the RD respectively.

9. The system as in claim 7 where a first MW is operatively connected to a proximal end of the RD and a second MW is telescopically retained within the RD and is operatively engageable with a distal tip of the RD and where movement of the first MW relative to the second MW causes a shortening or lengthening of a distance between the proximal and distal ends of the RD and causes an expansion or compression respectively of a diameter of the RD.

10. The system as in claim 9 where the second MW can be advanced and torqued relative to the RD and the second MW includes a DES distal to the MW, the DES engageable with the distal end of the RD.

11. The system as in claim 10 where the second MW includes a distal tip portion distal to the RD.

12. A system for relieving pressure and re-aligning an aspiration catheter (AC) in contact with a cerebral artery, particularly within a tortuous section of the cerebral artery comprising: a redirection device (RD) operatively contained within a microcatheter (MC), the RD self-expanding and having a microwire (MW) operatively connected to a proximal end of the RD wherein the RD is deployable and re-sheathable from a distal tip of the MC and wherein upon deployment the RD expands to engage with an inner wall of the cerebral artery and a distal tip of the AC to relieve contact pressure between the AC and cerebral artery and/or re-align the AC with the cerebral artery.

13. A method for redirecting and advancing an aspiration catheter (AC) past a cerebral artery at a bifurcation and retrieving a clot adjacent the bifurcation, the method comprising the steps of:
   a) conveying a redirection device (RD) operatively retained within a microcatheter (MC) through the AC to a distal tip of the AC, the RD having a push wire (PW) operatively connected to a proximal end of the RD wherein the RD is expandable relative to the size of the MC;
   b) conveying the MC and RD to a position beyond the distal tip of the AC and past a distal edge of the clot;
   c) withdrawing the MC relative to the RD to cause a distal tip of the RD to emerge from the MC and expand to engage with the clot and the distal tip of the AC and wherein contact of the RD with the AC relieves pressure on the distal tip of the AC preventing forward movement of the AC;
   d) when pressure has been relieved and/or the AC has been re-aligned with the cerebral artery, advancing the AC forward over the RD to a proximal edge of the clot; and,
   e) applying suction and withdrawing all of the RD, MC and AC.

* * * * *